United States Patent
Self et al.

(10) Patent No.: US 8,409,129 B2
(45) Date of Patent: Apr. 2, 2013

(54) APPARATUS FOR REDUCING CONTAMINATION OF SURGICAL SITE

(75) Inventors: Sean D. Self, Sugar Land, TX (US); Geoff A Marcek, Houston, TX (US); James M. Fowler, Jr., Houston, TX (US)

(73) Assignee: Nimbic Systems, Inc.

( * ) Notice: Subject to any disclaimer, the term of this patent is extended or adjusted under 35 U.S.C. 154(b) by 711 days.

(21) Appl. No.: 12/434,098

(22) Filed: May 1, 2009

(65) Prior Publication Data
US 2010/0280436 A1 Nov. 4, 2010

(51) Int. Cl.
*A61M 37/00* (2006.01)
(52) U.S. Cl. .............. 604/23; 604/24; 604/26
(58) Field of Classification Search .......... 604/23–24, 604/26
See application file for complete search history.

(56) References Cited

U.S. PATENT DOCUMENTS

| | | | |
|---|---|---|---|
| 3,610,238 A | 10/1971 | Rich | |
| 3,692,024 A | 9/1972 | Von Otto | |
| 3,719,136 A | 3/1973 | Criddle | |
| 3,820,536 A * | 6/1974 | Anspach | 128/202.13 |
| 3,881,477 A | 5/1975 | Von Otto | |
| 3,927,667 A | 12/1975 | Criddle | |
| 3,930,497 A * | 1/1976 | Krebs et al. | 128/853 |
| 4,140,105 A | 2/1979 | Duvlis | |
| 4,205,668 A | 6/1980 | Criddle | |
| 4,275,719 A | 6/1981 | Mayer | |
| 4,422,369 A | 12/1983 | Smets | |
| 4,438,763 A * | 3/1984 | Zablen | 128/845 |
| 4,921,492 A | 5/1990 | Schultz | |
| 5,015,243 A | 5/1991 | Schifano | |
| 6,513,529 B1 | 2/2003 | Kamen | |
| 7,207,977 B2 | 4/2007 | Thompson | |
| 7,252,089 B1 | 8/2007 | Birnbaum | |
| 7,276,051 B1 * | 10/2007 | Henley et al. | 604/304 |
| 2006/0206051 A1 * | 9/2006 | Hamilton | 604/24 |

OTHER PUBLICATIONS

Thore M, et al., Further bacteriological evaluation of the TOUL mobile system delivering ultra-clean air over surgical patients and instruments, Journal of Hospital Infection 63, 185-192 (2006).

* cited by examiner

*Primary Examiner* — Kevin C Sirmons
*Assistant Examiner* — Edelmira Bosques
(74) *Attorney, Agent, or Firm* — Tim L. Burgess, P.C.

(57) ABSTRACT

Apparatus and methods for protecting a patient from surgical site infection from airborne microbes during surgery. A sterile gas flow conditioning emitter for affixation onto an anatomical surface of a patient adjacent a site of incision is anatomically shape conforming for attaching a unidirectional coherent non-turbulent flow field of sterile gas substantially anatomically levelly on that anatomical surface and flowing the flow field in the direction of that site while essentially preventing ambient airborne particles from entering the interior of the flow field under the emitter to maintain the gas essentially sterile during passage over the site.

19 Claims, 25 Drawing Sheets

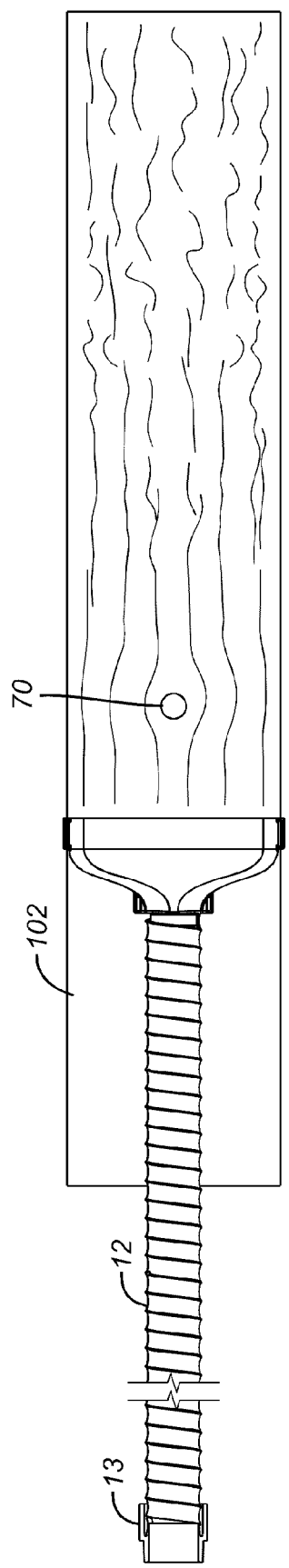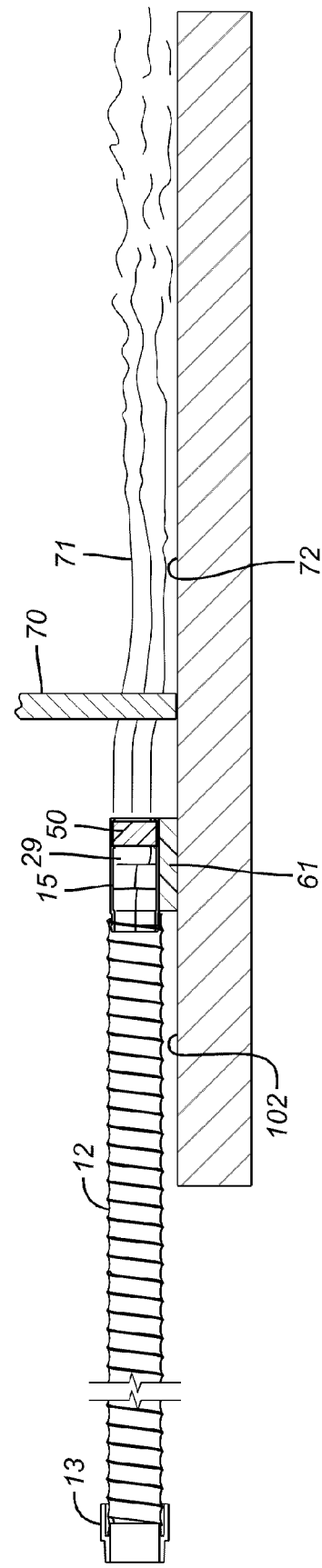

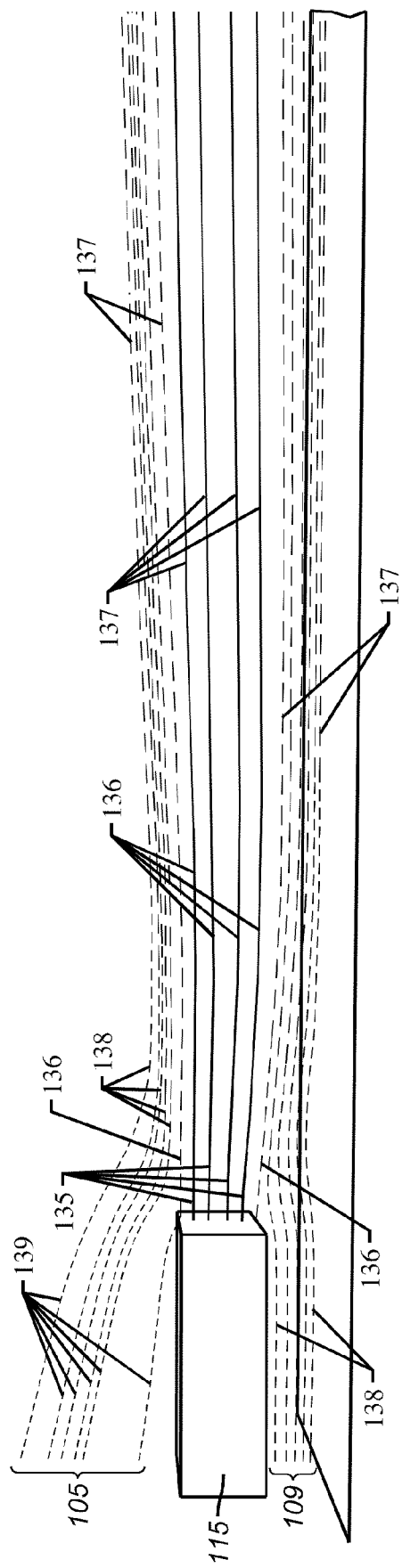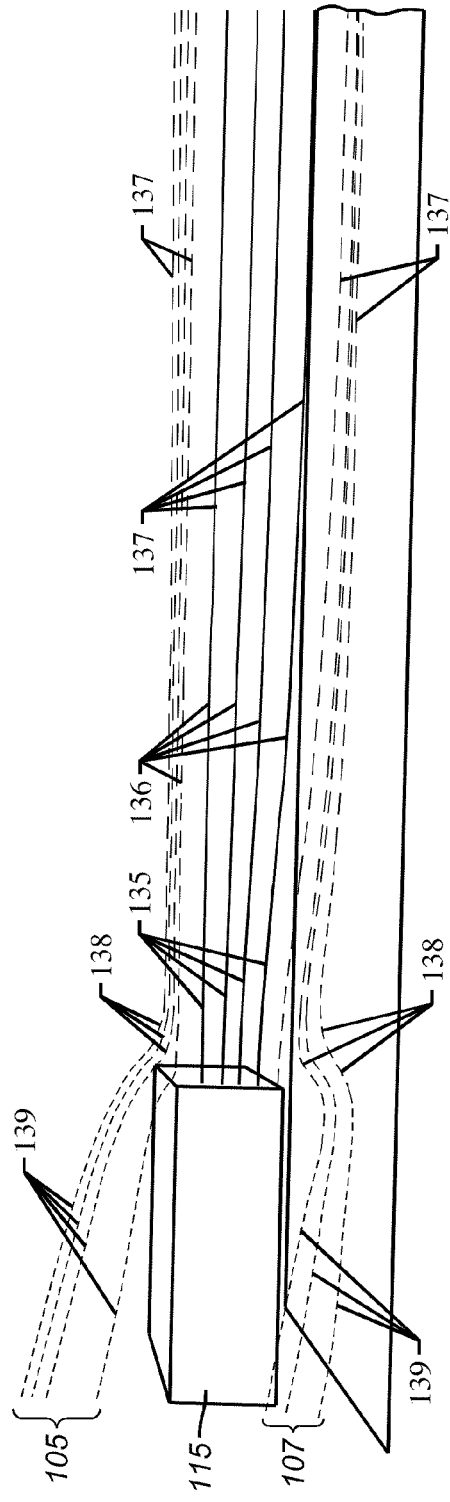

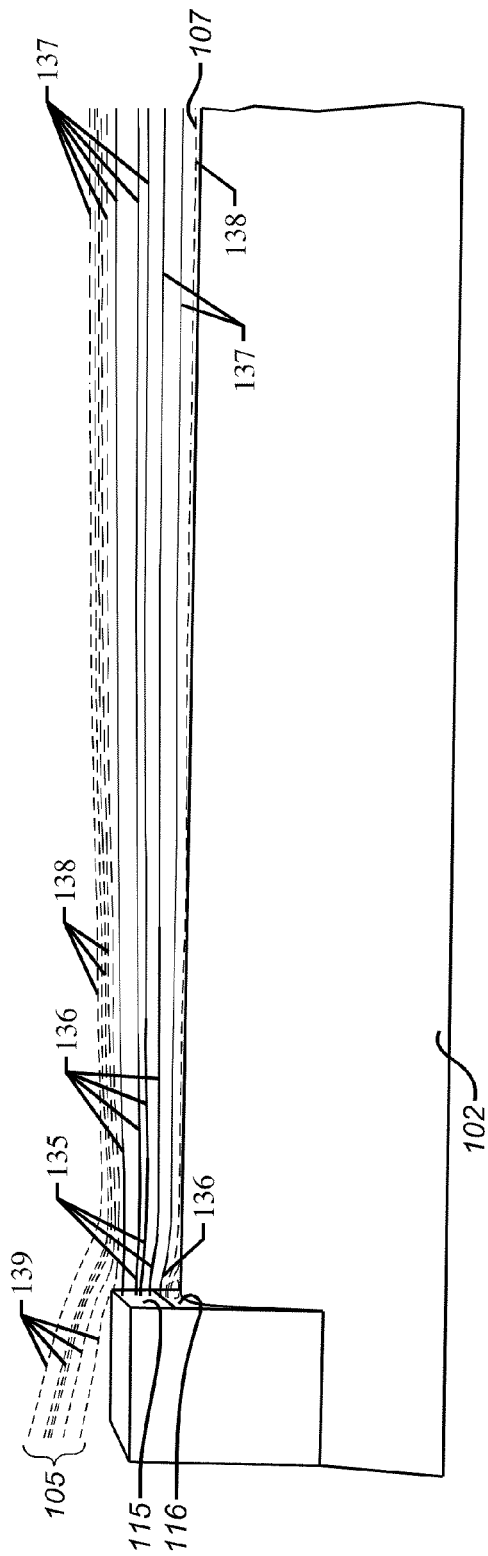
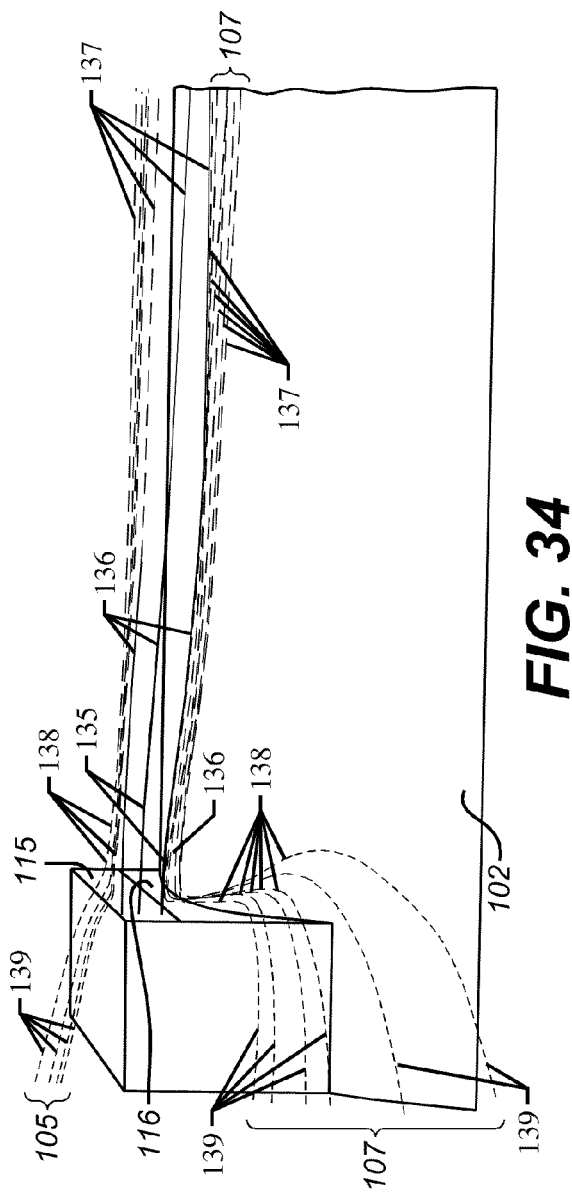
FIG. 33
FIG. 34

APPARATUS FOR REDUCING CONTAMINATION OF SURGICAL SITE

CROSS-REFERENCE TO RELATED APPLICATIONS

Not Applicable

STATEMENT REGARDING FEDERALLY SPONSORED RESEARCH OR DEVELOPMENT

Not Applicable

BACKGROUND OF THE DISCLOSURE

1. Field of the Disclosure

This invention relates to surgery, and more particularly, to air barriers used to reduce contamination of surgical sites.

2. Background Art

Hospital-acquired infections ("HAI"), also known as nosocomial infections, are a significant problem in modern healthcare systems. In 2002, approximately 1.8 million people contracted an HAI in U.S. healthcare facilities, and approximately 100,000 died as a result. HAI dramatically increases patient length of stay and cost and decreases hospital bed availability for other patients. The second most prolific cause of HAI is surgical site infections ("SSI"), which account for about 22% of all nosocomial infections. Hollenbeak C S, et al., *The clinical and economic impact of deep chest surgical site infections following coronary artery bypass graft surgery*, CHEST, 118 (2) (August 2000); *National Nosocomial Infections Surveillance (NNIS) System Report*, data summary from January 1992 through June 2004, issued October 2004, Centers for Disease Control and Prevention, publ. AMERICAN JOURNAL OF INFECTION CONTROL, 32, 470-85 (2004); Chu VH, et al, *Staphylococcus aureus bacteremia in patients with prosthetic devices: costs and outcomes*, THE AMERICAN JOURNAL OF MEDICINE, 118 (12) (December 2005); Klevens N R, et al., *Healthcare-associated infections and deaths in U.S. hospitals, 2002*, PUBLIC HEALTH REPORTS, 122, 160-166 (March-April 2007).

SSI infections mostly are "staph" infections, caused by the bacterium *Staphylococcus aureus*, which occurs harmlessly on human skin and frequently in the nose. If these bacteria gain access to a normally sterile space, such as in the capsule of a joint, they may multiply without resistance and create a huge infectious burden on the host. They often attach to prosthesis surfaces and multiply within dense aggregations called biofilms. Bacteria protected within biofilms are much harder to kill than individual isolated bacteria. SSI from bacterial invasion is particularly deleterious in procedures such as orthopedic joint arthroplasty, cardiovascular surgery, and neurosurgery. These types of infections develop deep within the body, are difficult to treat, and are devastating to patients. Antibiotics can't always penetrate tissues to reach bacteria that have taken root on implanted materials, and revision surgery on the infected joint is often necessary to eradicate the infection. Sometimes the infection will have caused so much bone loss that a second prosthesis replacement isn't an option, in which case the only option is fusing the bones together leaving the joint stiff and immobile and the patient in need of a mobility aid.

Airborne bacteria present in the operating room environment are a leading cause of SSI. A primary vector of microbial intrusion into the surgery site is direct precipitation from the atmosphere. Bacteria are generally 0.5-1 µm in size or larger and have a tendency to cluster together and attach to other larger particles. Airborne bacteria-carrying particles measure about 4 µm to 20 µm. Humans constantly shed skin scales in the 5-20 µm particle range into the atmosphere. Most current research regarding the vectors of airborne bacteria into the surgery site is based upon a study performed in 1982, Whyte W. et al., *The importance of airborne bacterial contamination of wounds*, JOURNAL OF HOSPITAL INFECTION, Vol. 3(2), 123-135 (June 1982). Whyte estimated that the source of about 98% of the bacteria present in a surgical wound was airborne. Studies indicate that controlling the presence of bacteria in the operating room atmosphere can reduce the risk of SSI.

Laminar flow operating rooms ("LFOR") were developed in the 1970's and 1980's to reduce the incidence of SSI from airborne bacteria. In a LFOR, clean air is introduced from filters in either the ceiling (vertical flow) or side wall (horizontal flow) at low speeds, e.g., 20 to 40 m/min (66 to 132 ft/min), to preserve laminar flow. The benefit thought to be achieved by LFOR air distribution is that filtered air flowing in laminar streams does not mix with contaminated air before reaching the surgery site, thus preventing airborne bacteria from reaching the surgery site. However, the ability of LFORs to accomplish this and prevent infections is qualified and debatable. Ritter M A, et al., *The operating room environment as affected by people and the surgical face mask*, CLINICAL ORTHOPEDICS, 111, 147-150 (September 1975); Franco J A, et al., *Airborne Contamination in Orthopedic Surgery. Evaluation of Laminar Air Flow System and Aspiration Suit*, CLINICAL ORTHOPAEDICS AND RELATED RESEARCH, Number 122 (January-February, 1977); Ritter M A, et al., *Comparison of Horizontal and Vertical Unidirectional (Laminar) Air-flow Systems in Orthopedic Surgery*, CLINICAL ORTHOPAEDICS, 129 (November-December 1977); Ritter M A, et al., *Laminar Air-Flow Versus Conventional Air Operating Systems: A Seven-Year Patient Follow-Up*, CLINICAL ORTHOPAEDICS, 150 (July-August 1980); Whyte W, et al., *The importance of airborne bacterial contamination of wounds*, Journal of Hospital Infection, 3(2), 123-135 (June 1982); Lidwell O M, et al., *Effect of ultraclean air in operating rooms on deep sepsis in the joint after total hip or knee replacement: a randomised study*, British Medical Journal, Vol. 285 (July 1982); Lidwell O M, et al., *Airborne contamination of wounds in joint replacement operations: the relationship to sepsis rates*, JOURNAL OF HOSPITAL INFECTION, 4 (2), 111-131 (June 1983); Horworth F H, *Prevention of Airborne Infection during Surgery*, ASHRAE TRANSACTIONS, 91(1b), 291-304 (1985); Horworth F H, *Prevention of Airborne Infections in Operating Rooms*, HOSPITAL ENGINEERING, 40 (8), 7-23 (1986); Charnley, J, *A clean-air operating enclosure*, THE CLASSIC, Number 211 (October 1986); Lidwell O M, et al., *Ultraclean air and antibiotics for prevention of postoperative infection. A multicenter study of 8,052 joint replacement operations*, ACTA ORTHOPAEDICA SCANDINAVICA, 58, 4-13 (1987); Van Griethuysen A J A, *Surveillance of wound infections and a new theatre: unexpected lack of improvement*, JOURNAL OF HOSPITAL INFECTION 34, 99-106 (1996); Ritter M A, Operating room environment, CLINICAL ORTHOPAEDICS & RELATED RESEARCH, 369, 103-109 (December 1999); Persson M, et al., *Wound ventilation with ultraclean air for prevention of direct airborne contamination during surgery*, INFECTION CONTROL AND HOSPITAL EPIDEMIOLOGY, 25 (4) (April 2004); Clarke M T, et al., *Contamination of primary total hip replacements in standard and ultra-clean operating theaters detected by the polymerase chain reaction*, ACTA ORTHOPAEDICA 75 (5), 544-548 (2004); Pereira M L, et al., *A Review of Air Distribution Patterns in Surgery Rooms under Infection Control Focus*, ENGENHARIA THERMICA (Thermal Engineering), 4 (2), 113-121 (October 2005); Miner A L, et al., *Deep Infection After Total Knee Replacement: Impact of Laminar Airflow Systems and Body Exhaust Suits in the Modern Operating Room, INFECTION CONTROL AND HOSPITAL EPIDEMIOLOGY, 28 (2), (February 2007); Pasquarella C, et al., *A mobile laminar airflow unit to reduce air bacterial contamination at surgical area in a conventionally ventilated operating theatre*, JOURNAL OF HOSPITAL INFECTION, 66 (4), 313-319 (August 2007).

While laminar flow air is clean when leaving the air vents in the wall or ceiling, it must traverse a significant distance in a room laden with contaminants and will entrain ambient particles in its flow. Overhead lights and staff leaning over the patient are regularly interposed between the clean air source and the surgery site, creating a direct vector for contaminants to compromise the patient. Recent studies have shown that the primary source of the airborne contamination in the operating room, assuming HVAC systems are properly designed and maintained, is the shedding of bacteria and particulate matter, such as skin scales bearing bacteria, by people present in the operating room, including personnel outside the sterile surgical field (circulating nurses, anesthesiologists, radiology technicians and other technicians). See e.g., Edmiston Jr. C E, et. al., *Molecular epidemiology of microbial contamination in the operating room environment: Is there a risk for infection-?*SURGERY, 138:573-582 (October 2005). In other words, the inclusion of surgical personnel and equipment within the air barrier may limit the ability of LFOR systems to reduce airborne microbes arising from those people and that equipment. Moreover, laminar flow operating theatres are uncommon and costly. Installing one laminar flow surgery room costs at least about $500,000, is a major construction project, and disrupts surgery room availability.

An alternative approach to LFOR systems has been to move a source of sterile air closer to the patient or the operating table. U.S. Pat. 3,820,536 (Anspach Jr. et al., 1974) describe bringing a high efficiency particulate air filter ("HEPA") blower up to an operating table and angling the blown air downwardly onto the patient. In a study, Thore M, et al., *Further bacteriological evaluation of the TOUL mobile system delivering ultra-clean air over surgical patients and instruments*, JOURNAL OF HOSPITAL INFECTION 63, 185-192 (2006), a freestanding mobile laminar flow clean air source was evaluated, similar to the device described in U.S. Pat. No. 3,820,536. The device was positioned approximately 2 m away from the surgery site at an elevation above and angled down toward the site and said to have delivered laminar flow HEPA air toward the surgical field. Since the device could be positioned closer to the surgery area than would be the case where the air source is built into the infrastructure of the room, it was thought that the contamination effect of room traffic would be reduced. During actual surgery, Thore et al. found that the device was ineffective after the air traveled further than approximately 1 m from the unit due to the room dynamics between the air source and the surgery site.

Others that have tried moving the source of sterile air closer to the patient or the operating table include Meyer as described in U.S. Pat. No. 4,275,719 (1981) and Smets as described in U.S. Pat. No. 4,422,369 (1983). Mayer described a pair of nozzles flat in cross section aligned on either side of an incision area (one nozzle to blow sterile air, the other to collect it) with the nozzles held in place with strips of tape. Smets described a system in which a curtain of sterile air is formed above a surgical table also using aligned blower and suction nozzles. A drape reaches from the lower edge of the blower nozzle to the surface of a table to prevent entrainment of ambient air beneath the blower nozzle. This arrangement set up a turbulent circulation under the blower nozzle. A nozzle in the shape of a flattened cone is placed on the surface of the table to flow sterile air into the circulation opposite the direction of flow of the overhead air curtain to neutralize disturbances caused by the gas curtain.

Other than LFOR's, the only solution finding its way into mainstream utilization has been body exhaust suits ("BES"), also developed in the 70's and 80's. Colloquially called a "space suit," these consist of a plastic helmet with a built-in filter over which a sterile hood with a view pane is placed to completely encapsulate the surgeon's face and neck. Contaminants from the surgeon's head region are captured and filtered before the air is exhausted back into the operating room. The ability of BES to prevent contamination of the surgery site is viewed as unproven. Franco J A, et al., CLINICAL ORTHOPAEDICS AND RELATED RESEARCH (1977), ibid; Der Tavitian J, et al., *Body-exhaust suit versus occlusive clothing—a randomized, prospective trial using air and wound bacterial counts*, JOURNAL OF BONE AND JOINT SURGERY (British), 85-B:4, 490-494 (2003); Miner A L, et al., INFECTION CONTROL AND HOSPITAL EPIDEMIOLOGY, ibid; Ritter M A, CLINICAL ORTHOPAEDICS & RELATED RESEARCH (2007), ibid. Body exhaust suits isolate the surgeon, not the patient. Moreover, typically, only surgical personnel working in the operating room within the surgical field (surgeons, surgical assistants and technicians, and scrub nurses) wear the suits during a surgery.

Beyond the mainstream LFOR and BES solutions, virtually no new technology has emerged and been generally adopted over the past 30-plus years to remove the source or cause of SSI, and even the LFOR and BES approaches to the SSI problem are rarely used outside of orthopedic joint replacement surgery because they are so costly and complicated. As a result, the incidence of SSI remains largely unabated. Innovations currently being pursued in research and industry to combat SSI infection have shifted primarily from preventive solutions for the operating room to post operative pharmaceutical solutions, directed to creating antibacterial drugs that would prevent infections from developing post-operatively and would mitigate the effects of infection once microorganisms enter the body. History is testament that drug resistant bacteria develop as a result of application of antibacterial drugs.

The root problem remains: how to prevent bacteria shed by personnel in the operating room from invading the surgical wound during surgery. A second part is how to solve the root problem in a way that can facilitate widespread adoption of the solution and by widespread adoption significantly combat and reduce SSI. For widespread adoption, the solution must not only be effective, it has to be cost effective, and it should be easy for surgeons and staff to implement. Yet, for more than 30 years since initial appreciation of the root cause of SSI, and despite urgent need and serious efforts of many dedicated professionals, scientists and engineers to address the root problem, SSI from operating room bacteria remains a serious unresolved health care issue.

The present invention is directed to the root cause of the SSI problem: effectively preventing bacterial invasion of a surgically created wound during the surgery; and is also directed to the second part of the problem: making the solution effective, inexpensive and easy to implement. The invention has particular advantage for surgical procedures involving deep, "clean" anatomical structure, for example, without limitation, orthopedic joint arthroplasty, pediatric ventricular shunt implantation, cardiac implant and vascular surgery, and long-duration procedures.

BRIEF DESCRIPTION OF THE DRAWINGS

FIG. 5 is a top view of an embodiment of an emitter assembly of FIGS. 3 and 4 placed on a surface 102, schematically depicting flow lines of a gas emitted from the emitter assembly.

FIG. 6 is a side sectional view of an embodiment of an emitter assembly of FIGS. 3 and 4 placed on surface 102, schematically depicting flow lines of a gas emitted from the emitter assembly.

FIG. 21 is a depiction of the flow trace elements in a vertical plane through the center of the emitter of FIG. 26.

FIG. 22 is a depiction of the flow trace elements at the lateral edge of the emitter of FIG. 17.

FIG. 33 is a depiction of the flow trace elements in a vertical plane through the center of the emitter of FIG. 32.

FIG. 34 is a depiction of the flow trace elements at the lateral edge of the emitter of FIG. 32.

DETAILED DESCRIPTION OF EMBODIMENTS

Figure 1:
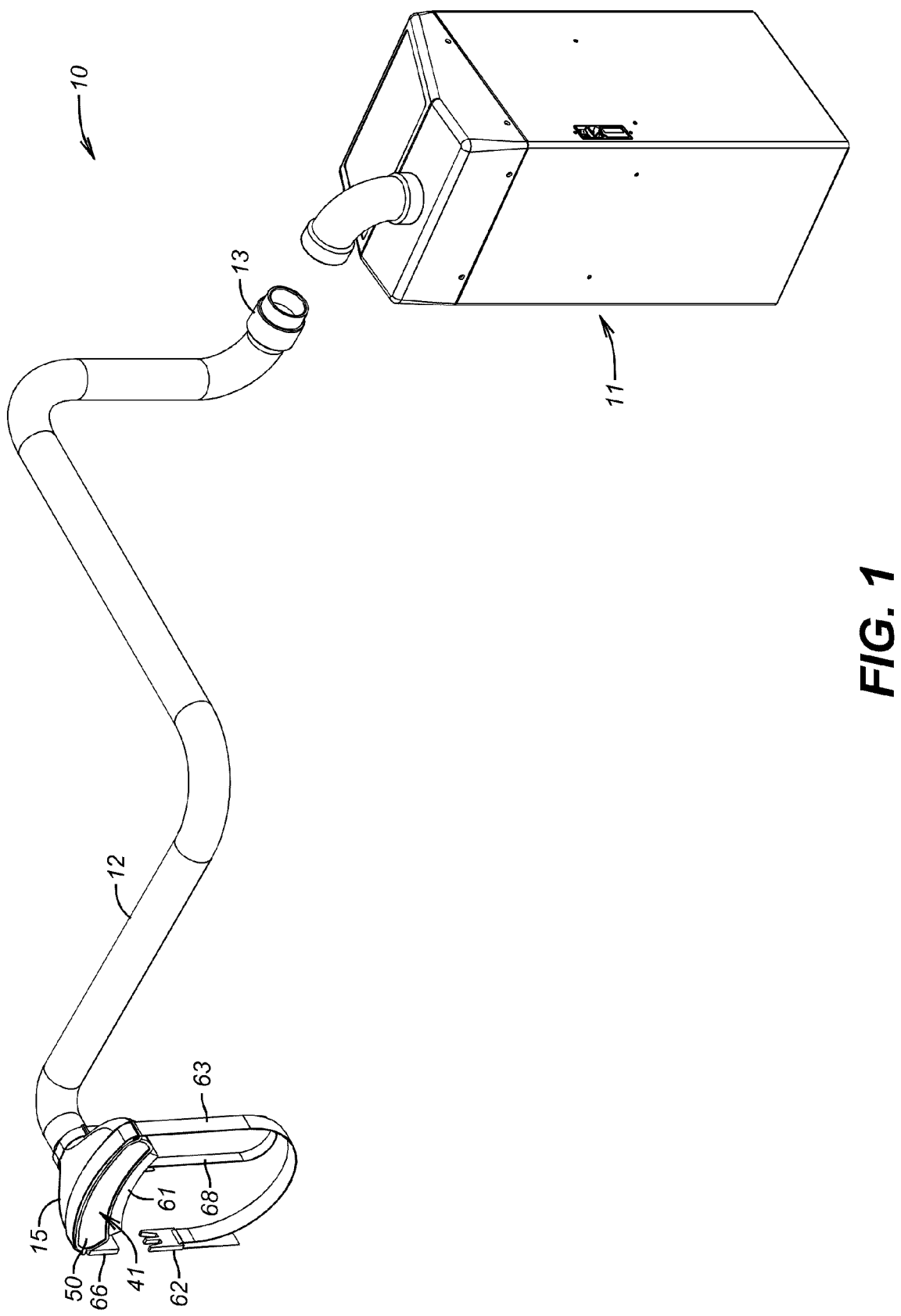
FIG. 1. is a perspective view of apparatus including an embodiment of a flow conditioning gas emitter in accordance with the invention.

In the following detailed description of embodiments, reference is made to the accompanying drawings, which form a part hereof and in which are shown, by way of illustration, specific embodiments in which the invention may be practiced. Specific details disclosed herein are in every case a non-limiting embodiment representing concrete ways in which the concepts of the invention may be practiced. This serves to teach one skilled in the art to employ the present invention in virtually any appropriately detailed system, structure or manner consistent with those concepts. It will be seen that various changes and alternatives to the specific described embodiments and the details of those embodiments may be made within the scope of the invention. Because many varying and different embodiments may be made within the scope of the inventive concepts herein described and in the specific embodiments herein detailed without departing from the scope of the present invention, it is to be understood that the details herein are to be interpreted as illustrative and not as limiting.

The various directions such as "upper," "lower," "bottom," "top," "back," "front," "perpendicular", "vertical", "horizontal," "length" and width" and so forth used in the detailed description of embodiments are made only for easier explanation in conjunction with the drawings to express the concepts of the invention. The elements in embodiments may be oriented differently while performing the same function and accomplishing the same result as obtained with the embodiments herein detailed, and such terminologies are not to be understood as limiting the concepts which the embodiments exemplify.

As used herein, the use of the word "a" or "an" when used in conjunction with the term "comprising" (or the synonymous "having" or "including") in the claims and/or the specification may mean "one," but it is also consistent with the meaning of "one or more," "at least one," and "one or more than one." In addition, as used herein, the phrase "connected to" means joined to or placed into communication with, either directly or through intermediate components.

Private research in which one of us participated found that the number of airborne particles 10 μm or larger in size present in an operating room during actual hip and knee joint arthroplasties conducted under carefully controlled testing, but without benefit of our invention, was associated with the number of bacterial colony forming units (CFU) grown from air sampled within the sterile field approximately 40 cm from the surgical incision at the surgical site during the arthroplasties. (Reference herein to 10 μm particles is to be understood to mean 10 μm and larger.) The number of 10 μm airborne particles was also associated with the number of surgical staff present in the operating room. The finding that the number of 10 μm particles was correlated with the number of CFU at the surgical site supports airborne particulate contamination of the wound as a source of post-operative infection in joint arthroplasty. When the density of 10 μm particles in these operating rooms exceeded 300 particles/ft$^3$ in any 10-min interval, the average CFU count at the surgical site exceeded 25 CFU/m$^3$ during that interval. It is likely that the correlation of larger particles (10 μm and larger) with CFUs observed in this study was attributable to the larger particles being capable of carrying bacteria. Thus a device and methodology that would exclude airborne particles 5 μm and larger from the surgical field would help protect the surgical site from bacterial contamination.

In accordance with the present invention, the embodiments and methods described herein work to create a figurative "cocoon" of essentially sterile gas immediately overlaying a surgical opening, sometimes called a surgical wound, to protect the wound from contamination by ambient airborne particles. The cocoon is a localized flow field of coherent non-turbulent essentially sterile gas. The word "gas" is used to include mixtures, compounds and elemental gases that are not deleterious for surgical use, and includes air, mixtures of air with vapors or other gases having a sterilant property, i.e., having active properties that help negate viability of microbes, such as hydrogen peroxide or ozone, mixtures of air with vapors that have analgesic properties, and mixtures of air with low concentrations of one or more denser inert gases, such as nitrogen or argon, to displace ambient air. Air is mostly used as a source gas for scrubbing by a HEPA device to provide a sterile gas because it is free of added cost. The term "sterile gas" means gas from which 90% or more of ambient airborne particulates 0.3 μm and larger have been removed. The term "essentially sterile gas" is used to mean a gas containing 90% or less of particles 5 μm and larger than in ambient air in the room where the methods and embodiments are employed.

The "cocoon" of essentially sterile gas is created to be located beneath both surgical staff (who are usually leaning over the incision) and the overhanging operating room equipment, with the result that surgical staff, operating room equipment and others in the operating room, who are a source of airborne particles that may carry microbes, are positioned outside the protective cocoon. As used herein, "microbes" includes bacteria, fungal spores and other microorganisms present in the ambient atmosphere in an operating room.

The cocoon is created by taking advantage of boundary layer surface effects. Coanda described an effect in U.S. Pat. No. 2,052,869 (1935), now called the Coanda Effect, which acted on the observation that when a stream or sheet of gas is issued at high velocity through an orifice into an atmosphere of another gas, a suction effect will be induced at the point of discharge, drawing forward the adjacent gas in the atmosphere. Coanda showed that if flow of adjacent gas were checked on one side of the orifice, the flow emergent from the orifice would be diverted to the side where the check is imposed. In simple terms, the Coanda Effect is that a jet of gas into an atmosphere of another gas attaches to an adjacent wall. According to traditional fluid dynamics, when a fluid (gas or liquid) moves along a solid surface (a wall, without implication of verticality), frictional forces drag along a thin layer of the fluid adjacent the surface due to the viscosity of the fluid. This thin layer is called the boundary layer. The boundary layer generally exists in one of two states: laminar, where fluid elements remain in well-ordered nonintersecting layers, and turbulent, where fluid elements totally mix. Turbulence develops when the laminar stream filaments immediately adjacent the surface separate from the surface. The state of the boundary layer, in the absence of disturbing influences, is directly related to the speed of the fluid over the surface and the distance along the surface-first it is laminar, and then it changes to turbulent as the speed or distance increases. This behavior is described by a parameter known as the Reynolds number (Re), a non-dimensional number equal to the product of the velocity (v) of the fluid moving over the surface, the density (ρ) of the fluid and a representational length (l) divided by the fluid viscosity (μ). This relationship is defined by the formula: $Re = v\rho l/\mu$.

In accordance with the present invention, the cocooned protection of the surgical site is achieved by attaching a unidirectional coherent non-turbulent flow field of essentially sterile gas substantially anatomically levelly on an anatomical surface of a patient adjacent the site of a surgical incision, and maintaining that flow field substantially anatomically levelly along the surface anatomy of the patient up to and through the incision site while keeping the gas essentially sterile. The flow field sweeps ambient airborne particles along the outer layers of the flow field cocoon away from the interior layers over the surgical wound. The flow field transitions to turbulent flow past the field of effect disbursing ambient particles away from the operating table.

In order to accomplish this, there is provided apparatus for affixation onto an anatomical surface adjacent a site of incision typical for a type of surgery to protect a patient from surgical site infection during the surgery. The apparatus comprises anatomically shape conforming means for attaching a unidirectional coherent non-turbulent flow field of sterile gas substantially anatomically levelly on said anatomical surface flowing in the direction of the incision site and preventing ambient airborne particles from entering the interior of the flow field under said means sufficiently to maintain said gas essentially sterile at the incision site. Embodiments of apparatus disclosed herein provide the means for accomplishing the stated protection.

In one embodiment, the apparatus comprises a flow conditioning anatomically shape conforming emitter of a sterile gas for attaching a unidirectional coherent non-turbulent flow field of sterile gas substantially anatomically levelly on the anatomical surface of a patient flowing in the direction of the site and preventing ambient airborne particles from entering the interior of the flow field under the emitter to maintain the gas essentially sterile during passage over the site. In an embodiment, the emitter has an undersurface so matching the shape of the anatomical surface that, when the emitter is affixed to the anatomical surface, ambient airflow is substantially completely prevented from penetrating underneath the emitter and entering the interior of the coherent non-turbulent flow field. In an embodiment, the emitter has an outlet for the sterile gas having: a dimension of height and width, a lower margin essentially uniformly along the outlet width equidistant to the undersurface, and a dimension of height between the outlet and the undersurface such that when the emitter is affixed onto the anatomical surface the gas flow from the outlet is substantially anatomically level with the anatomical surface of the patient across the width of the outlet. In an embodiment, the mentioned portion is deformable to provide the mentioned dimension of height.

There is thus enabled and provided a method of performing surgery on a patient comprising making a surgical incision in a portion of a patient's anatomy covered by an attached unidirectional coherent non-turbulent flow field of essentially sterile gas, the field originating from a substantially anatomically level position adjacent to the site of incision under flow conditions providing a boundary layer of the flow field attached to the anatomical surface for a distance at least extending through the surgical site. "Non-turbulent" encompasses both well-ordered coherent laminar flow and still coherent flow transitioning from well-ordered flow toward (but not yet in) the turbulent state. An instrument, prosthesis, or surgeon or surgical assistant's fingers or hand inserted into the flow field cocoon over the surgical site may divert laminar flow around the inserted member that transitions through a non-turbulent transitional stage into a turbulent flow regime downstream from the inserted member, but the turbulent flow will be past the surgical opening. Accordingly, coherent non-turbulent flow is maintained through the site of the surgical incision very effectively reducing the presence of airborne particulate and microbes inside the cocoon at the surgical site and concomitantly reducing the risk of surgical site infection.

Forming and maintaining a unidirectional coherent non-turbulent flow field of essentially sterile gas comprises (i) having a supply of sterile gas, (ii) forming that gas into a unidirectional coherent non-turbulent flow field, (iii) placing that sterile flow field substantially anatomically levelly on an anatomical surface of a patient adjacent the site of a surgical incision, and (iv) flowing the field substantially anatomically levelly along the surface anatomy of the patient up to and through that site while keeping essentially sterile the interior portion of that flow field that will come into contact with the wound created by the surgical incision. Keeping the gas essentially sterile involves substantially completely preventing ambient airborne particles 5 µm or larger from invading the interior of the flow field. Airborne particles 5 µm or larger are substantially completely prevented from entering the interior portion of the flow field when the content of particles 5 µm and larger in the airflow over the surgical opening is 90% or less than in ambient air. While the gas flow field sweeps ambient particles along its edges preventing their entry into the cocoon from above, the embodiments also guard against their infiltration from below adjacent the surface on which the cocoon of sterile air is attached.

Accordingly, there is provided a method for reducing the risk of intrusion of ambient airborne bacteria into a surgical incision during surgery, comprising: affixing a flow conditioning emitter of a unidirectional coherent non-turbulent flow field of sterile gas onto an anatomical surface adjacent a site of the incision, the emitter having an undersurface so matching the shape of the anatomical surface that, when the emitter is affixed to the anatomical surface, ambient airflow is substantially completely prevented from penetrating underneath the emitter and entering the interior of the coherent non-turbulent flow field; supplying sterile gas to the emitter; conditioning the sterile gas into a unidirectional coherent non-turbulent flow field emergent from the emitter; attaching that sterile flow field substantially anatomically levelly on an anatomical surface of a patient adjacent the site of a surgical incision; and flowing the attached field substantially anatomically levelly along the anatomical surface of the patient in the direction of the incision for a distance at least immediately past the incision.

The unidirectional coherent non-turbulent flow field is formed in and flowed from an anatomically shape conforming gas emitter, specifics of which are described below. As will be described below, we employ a hose leading from a HEPA device to a flow conditioning emitter formed in accordance with our invention. The hose is constructed of a material providing it flexibility and maneuverability allowing the emitter to be placed substantially anatomically levelly on a portion of a patient's surface anatomy adjacent a site on the patient's anatomy where an incision is to be made. Sterile gas received in the emitter from the hose is turbulent, and the emitter must transform that turbulent condition into a unidirectional coherent non-turbulent flow (this transformation is what is meant by the term "flow conditioning"). A diffuser as described in more detail below creates a uniform backpressure along its internal surface that allows the gas to emerge from the diffuser of the emitter at a constant velocity along its external surface. Flow rates from the HEPA device are adjusted to maintain the backpressure created by the diffuser that allows the gas to emerge from the diffuser in unidirectional coherent non-turbulent flow at a selected constant velocity. The velocities mentioned herein are the velocities of the gas emergent from the diffuser in the emitter.

We use the phrase "substantially anatomically level" in a specific way in relation to placement and maintenance of the flow conditioned gas. The word "level" has a height attribute. It means the lowest part of the unidirectional coherent non-turbulent sterile gas flow field is not so much higher than the anatomical surface that the lowest part of the emitted sterile gas flow field does not attach to and form a boundary layer on the anatomical surface adjacent the emitter. In addition the word "level" does not refer to the horizon parallel to an operating table; it refers to the direction of flow being generally horizontal with the anatomical surface of a patient adjacent the site where the surgical opening will be created. (That surface may or may not be at an angle to the horizon during the surgery, and indeed the anatomy on which that surface resides may be moved from one position to another during surgery; for non-limiting example, during a knee or hip replacement with a prosthesis, the anatomical surface may be on the thigh, which may or may not be horizontal with the operating table, and the thigh may be moved during surgery to manipulate the joint.) The words "anatomically level" or "anatomically levelly" also imply a contour or profile attribute. The relevant ultimate contour is a contour of an anatomical surface transverse to the direction of flow of the coherent non-turbulent gas field, and the relevant controlling contour is the contour of the orifice of the emitter, which in accordance with the invention, is a contour designed to conform generally to an anatomical surface contour where the emitter ultimately will be placed. Thus "anatomically level" means the flow is level (as defined above) in the direction of flow for the width of the orifice of the gas emitter from which the flow field emerges. "Substantially" as a modifier of "anatomically level" means that if not exactly anatomically level, the anatomically level placement is close enough to horizontal and close enough to the anatomical surface to achieve attachment of a boundary layer of unidirectional coherent non-turbulent flow of sterile gas toward the surgical site along substantially the contour width of the emitter.

The term "anatomical surface" is used in reference to a surface adjacent where a surgical incision is to be made. In surgical procedures, the site of an incision is typically prepared first by painting the surgical area with an iodine or other bactericidal solution, followed by laying over the area a film the underside of which is coated with an adhesive and bactericide, and then by placing over the film a disposable drape having a window for the incision work and next by adhering the drape to the film by an adhesive on the underside borders of the window. Once prepared, an incision is made within the window through the film into the painted skin. When we speak about placing an anatomically shape conforming emitter on an "anatomical surface" adjacent to where an incision is to be made, we do not imply that the emitter is necessarily applied directly to the skin; rather we mean the anatomical surface to be a surface adjacent where an incision is to be made that generally conforms to the shape of the anatomy adjacent where an incision is to be made. Accordingly, the emitter may be placed on the skin or on film adhered to the skin within the drape window or even on the surface of the drape adjacent the window where the drape is adhered to the film, provided the emitter is substantially anatomically levelly placed on that surface. By adjacent to where an incision is to be made, we mean that the emitter is placed close enough to the site of the incision for the flow field established in accordance with the invention to reach through the site of the incision.

The critical Reynolds number at which gas flow becomes turbulent for flow over a theoretical flat plate (wall) is generally $1\times10^5$ (100,000). In the methods and embodiments of this invention, the anatomical surface of the patient supplies the wall, albeit not a flat plate. As explained above, the operative variables for calculation of a Reynolds number to predict the character of flow are distance and velocity of the gas (density and viscosity of the gas are normally givens). Thus, distance from gas emitter to the site for incision is a factor in maintaining the flow field unidirectional, coherent and non-turbulent. The field of effect of the essentially sterile coherent non-turbulent flow stream need not be long, and in an embodiment is approximately half a meter long or less. Most human anatomies do not have portions for incision more distant than a half meter from any anatomical surface where an emitter embodiment could be placed, for example, the distance along the thigh from hip to knee will not exceed about half a meter (about 20 inches) except in the very tallest people. Thus spacing of the emitter from the site of incision ordinarily will be less than 20 inches, suitably 12 inches or less, for example, 6 inches or even 3 inches. At a spacing of 6 inches separating the emitter from the site of incision, the characteristic of flow over a flat plate predicted using the formula for calculation of Reynolds number should be coherent and non-turbulent for velocities of about 800 ft/min (Re=40,500), but at that velocity would be turbulent (Re=121,700) at a spacing of 18 inches. At a spacing of 18 inches, flow may be coherent and non-turbulent under ideal conditions for velocities theoretically of 400 ft/min (Re=60,800) to 500 ft/sec (Re=75,100). However, these are theoretical conditions; the actual anatomical surface is not a flat plate and may have some slight waviness or surface roughness or both. At 6 inches from an emitter flowing air unidirectionally at a velocity of 350 ft/min (5.83 ft/sec) parallel to a flat plate, the Reynolds number is Re=17,700 and will be expectably fully laminar applied to the anatomical surface of a patient. A relatively moderate flow velocity maintained substantially constant in a range from about 1 m/sec to about 2 m/sec, suitably from about 180 ft/min to about 400 ft/min, provides satisfactory results, and may be slower or faster according to the particular emitter and the particular application keeping in mind the principles explained herein.

Accordingly, in an embodiment of the invention, there is provided a method of protecting a patient from surgical site infection of an incision during surgery, comprising conditioning a supply of sterile gas into a unidirectional coherent non-turbulent flow field, attaching that sterile flow field substantially anatomically levelly on an anatomical surface of a patient adjacent the site of a surgical incision and flowing the attached field substantially anatomically levelly along the anatomical surface of the patient in the direction of the incision for a distance at least immediately past the incision while restricting ambient airborne particles from entering the interior of the flow field that comes into contact with the incision.

In an embodiment, flow conditions are used that cause the flow field to separate from the anatomy of the patient and become turbulent approximately half a meter (approximately 20 inches) from the emitter. With this, ambient particles 0.5 µm and larger including any carrying microbes are intercepted and swept along the peripheries of the flow cocoon until past the approximately half meter distance from the emitter, where, as the field of flow transitions to a turbulent flow regime, the particles are dispersed by the turbulence away from the operating table and away from sterilized equipment downstream from the surgical site rather than remaining in a coherent flow passing down the table over sterilized equipment which the particles might contaminate. Theoretically (flat smooth surface), for an emitter gas velocity of 400 ft/min (6.67 ft/sec), at 24 inches from the emitter, the Reynolds number=81,100 at which flow is likely transitioning toward turbulence. Thus in use on a patient about half a meter is a reasonable approximation and is borne out by the experimental data described below.

In an embodiment, a supply of sterile gas is conditioned into a unidirectional coherent non-turbulent flow field having a velocity in the range from about 180 to 400 ft/min and flowed at a rate of from about 10 ft$^3$/min to 50 ft$^3$/min, suitably from about 15 ft$^3$/min to about 45 ft$^3$/min, and in a particular embodiment, from about 20 ft$^3$/min to about 43 ft$^3$/min in a flow field extending a distance in the range of from about 3 inches to about 20 inches.

An anatomically shape conforming emitter is used to perform the functions of (a) forming a unidirectional coherent non-turbulent flow field of sterile gas, (b) placing that flow field substantially anatomically levelly onto an anatomical surface, and (c) restricting ambient airflow from infiltrating the interior of the flow field and potentially contaminating the originally sterile gas that will come into contact with the surgical wound. An anatomically shape conforming emitter is one that has (a) a flow orifice or outlet the lower margin or boundary of which is essentially uniformly along its width equidistant to the undersurface of the emitter coming into contact with the anatomical surface where the emitter body is to be placed, (b) an undersurface so matching the shape of the anatomy where the emitter body is to be placed that ambient airflow is substantially completely prevented from penetrating underneath the emitter and entering the interior of the coherent non-turbulent flow emergent from the emitter outlet, and (c) a portion under the outlet of such height when applied and attached to an anatomical surface that flow emergent from the outlet immediately above that portion is substantially anatomically level with the anatomical surface of the patient across the width of the outlet. The height of the portion under the outlet may be adjustable, for example, that portion may comprise a deformable material that compresses when the emitter is applied and attached to the anatomical surface so that the height of that portion of the emitter does not exceed a height that would interfere with the emitter being substantially anatomically level with the relevant anatomical surface of the patient.

The anatomically shape conforming property for the emitter may be supplied, as in the embodiments described in detail below, with a combination of (a) a preformed rigid molded emitter body that generally conforms to a typical shape of an anatomical surface where the emitter is most likely to be placed for a particular type of surgery, and (b) a shape conformable material affixed to the underside of the molded body to provide a barrier substantially completely preventing infiltration of ambient airflow underneath the emitter. The shape conformable material is sufficiently adaptive to the specific shape and size of the anatomical surface of the particular patient where the generally shaped emitter is placed when the emitter body is affixed to the anatomical surface that ambient airflow is substantially completely prevented from penetrating underneath the emitter and entering the interior of the coherent non-turbulent flow over the surgical opening. Ambient airflow from underneath the emitter is determined to be substantially completely prevented when the content of particles 5 µm and larger in the airflow over the surgical opening is 90% or less than in ambient air.

Alternatively to forming a rigid molded emitter body, an anatomically shape conforming emitter may be manufactured of a pliable or malleable material, for example, a synthetic plastic silicone, that is shaped at the time of a surgery to specifically adapt to the particular surface contour of a patient where the emitter is to be placed yet maintain a flow outlet essentially uniformly along its width equidistant to the undersurface of the emitter coming into contact with the anatomical surface where the emitter body is to be placed. Other alternatives giving tangible form to the concepts of the invention may be formed with flexible fabric or plastic enclosures having an inlet and having an emitter outlet maintained to predetermined shape by stiffeners. These alternatives would comply with the concepts of our invention so long as they are capable of providing the unidirectional coherent non-turbulent flow conditions and substantially anatomical level flow field placement, and substantially completely preventing ambient air from penetrating beneath the emitter when applied to the anatomical surface of the patient, such as by using a barrier-forming adhesive or a supplemental shape conformable material affixed to the emitter underside.

Having now explained the concepts of our invention and in general how to apply them with an anatomical shape conforming emitter, we now describe in detail specific embodiments of anatomical shape conforming emitters that employ these concepts.

Referring in a first particular to FIG. 1, numeral 10 indicates one embodiment of the invention for use with a source 11 of sterile air. Apparatus 10 when connected to the source 11 of sterile gas establishes a three-dimensional flow field of substantially coherent non-turbulent flow of sterile gas layering a site on a patient's anatomy where a predetermined surgery is to be performed, to protect the site from ambient airborne particles during the surgery. Apparatus 10 comprises a hose 12 for attachment distally, at connector 13, to a high efficiency particulate air filter ("HEPA") source 11 capable of removing at least 90% of air borne particulates 0.3 micrometers and larger in diameter, and proximately, at connector 14, to an anatomically shape conforming emitter assembly 15. Hose 12 is constructed and formed of a material providing it flexibility allowing emitter assembly 15 to be placed substantially anatomically levelly directly on a portion of a patient's surface anatomy 102 adjacent a site on the patient's anatomy. This placement in concert with properly maintained flow conditions causes the surface of the patient to form the wall or base of a flow field for coherent non-turbulent sterile gas in which the boundary layer of the flow field can adhere to the surface of the patient.

Emitter assembly 15 comprises a housing 28 having an inlet 33 and an outlet 41 and enclosing a chamber 29. In the embodiment, the distance between the outlet of the housing and the surface of the body anatomy is minimized along the entire width of the outlet of the housing. To accomplish this, the physical shape of the housing is designed to match the anatomy specific to the surgery. For example, in hip replacement surgery, the anatomy of the patient at and near the hip is approximately a cylinder. Therefore, as in the embodiment of the emitter assembly of FIGS. 1-4 and 7-8, the lower part of the housing has an incurvate shape to minimize the distance from outlet 41 to the anatomical surface 102 across the entire width of outlet 41.

The depicted embodiments including the simulated embodiments used in the computer simulations all have an incurvate undersurface, as is suitable for application of the emitter to a hip or on a leg or other round portion of the anatomy. However, an emitter providing the functions of (a) forming a unidirectional coherent non-turbulent flow field of sterile gas, (b) placing that flow field substantially anatomically levelly onto an anatomical surface, and (c) restricting ambient airflow from getting into the interior of the flow field and potentially contaminating the originally sterile gas, can also be used where the anatomical surface has only a slight outward curvature, at least in a lean person, such as on the abdomen or chest, and for an double bowed anatomical surface, such as transversely to the spine across the back, a double bow shaped outlet would be used. The outlet is wide and tall enough to produce a flow field that effectively encompasses the site of the incision.

Figure 2:
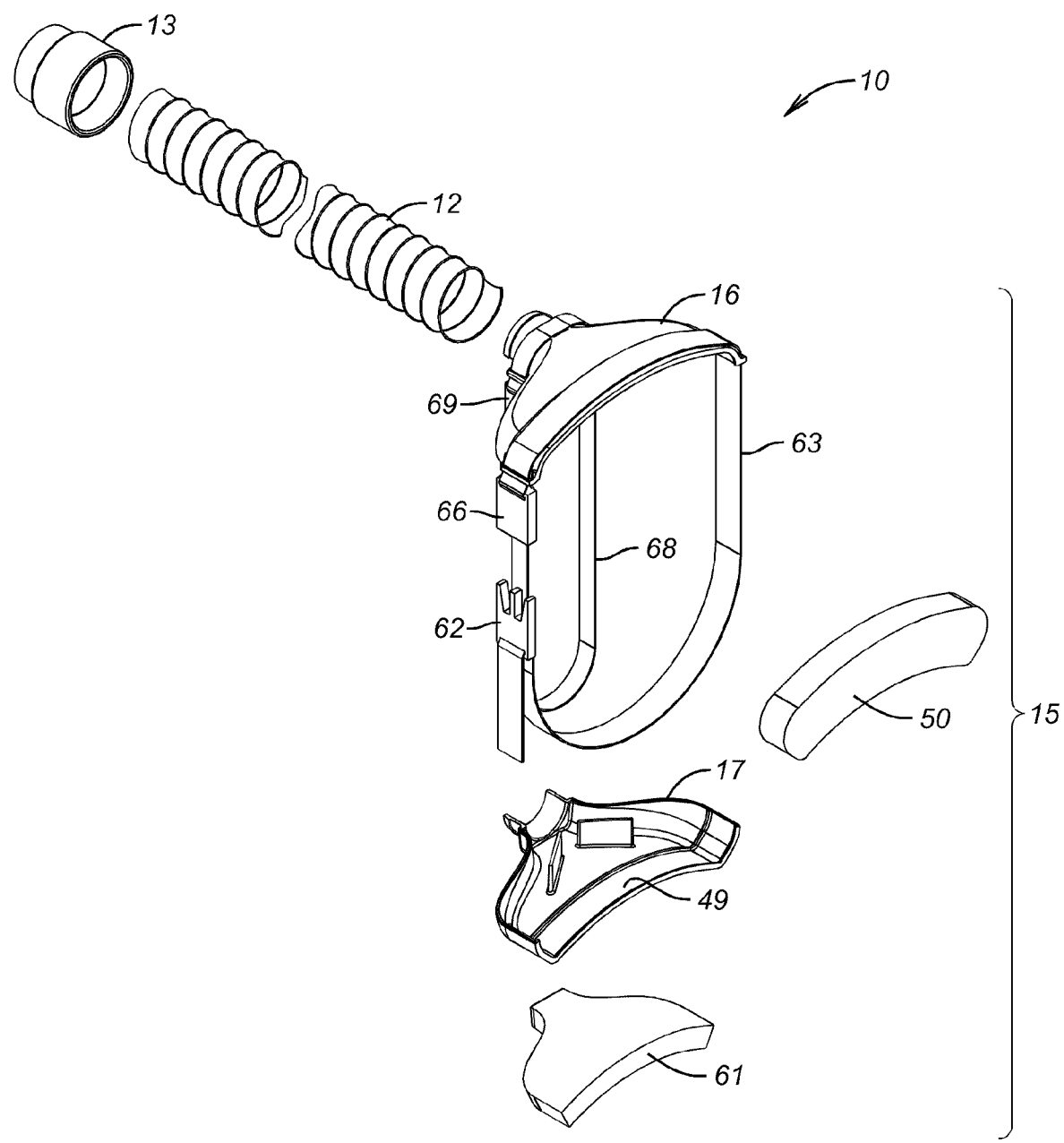
FIG. 2 is a perspective view including an exploded view of the flow conditioning gas emitter of FIG. 1.
Figure 3:
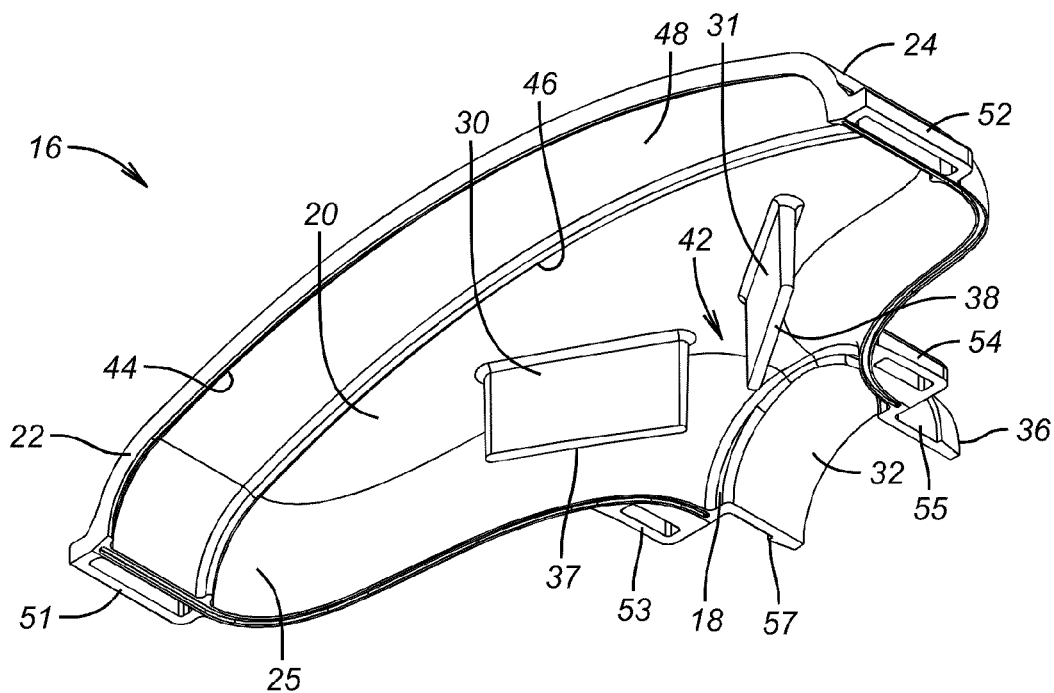
FIG. 3 is an isometric view of the upper half of the casing of an emitter assembly of FIGS. 1 and 2.
Figure 4:
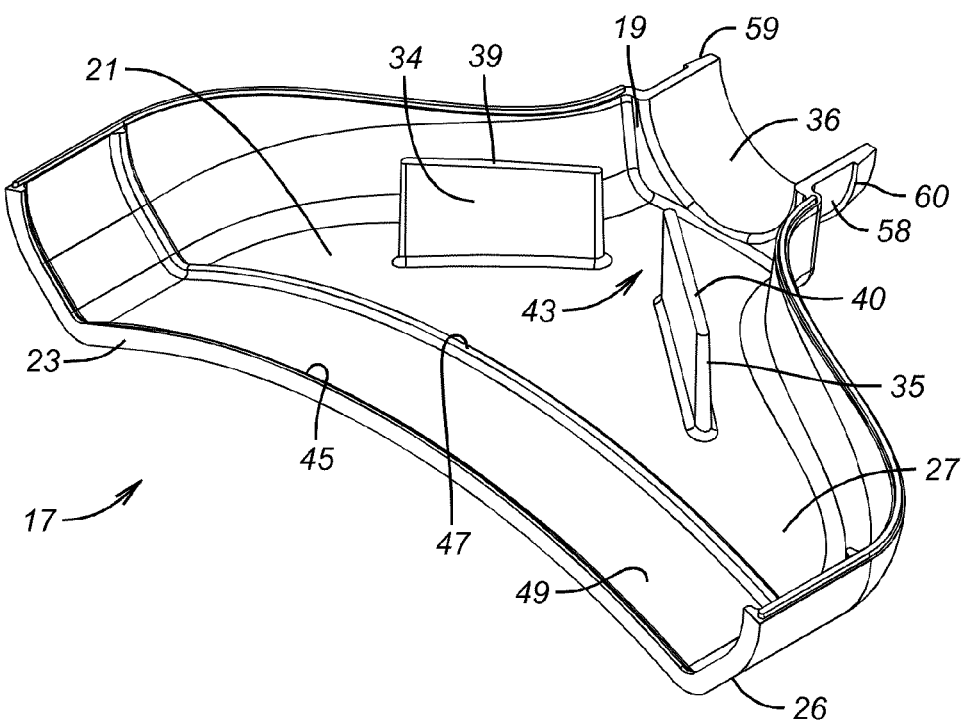
FIG. 4 is an isometric view of the lower half of the casing of the emitter assembly of FIGS. 1 and 2.
Figure 7:
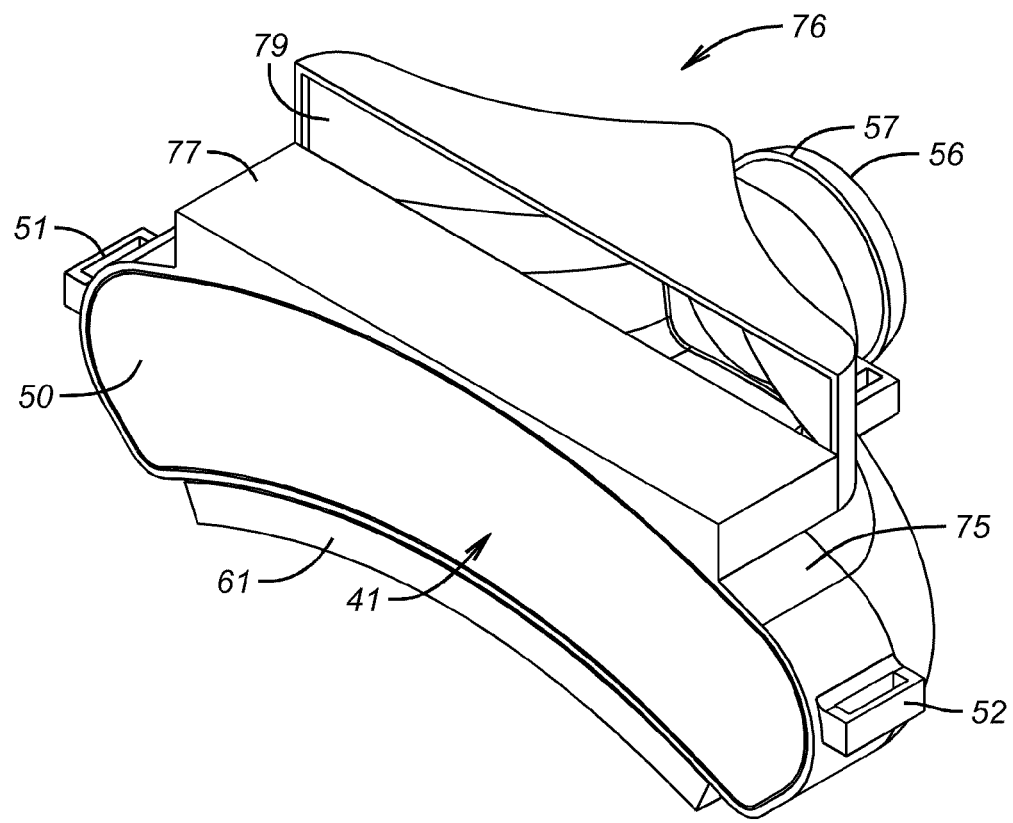
FIG. 7 is an isometric view of another emitter assembly in accordance with the invention.
Figure 8:
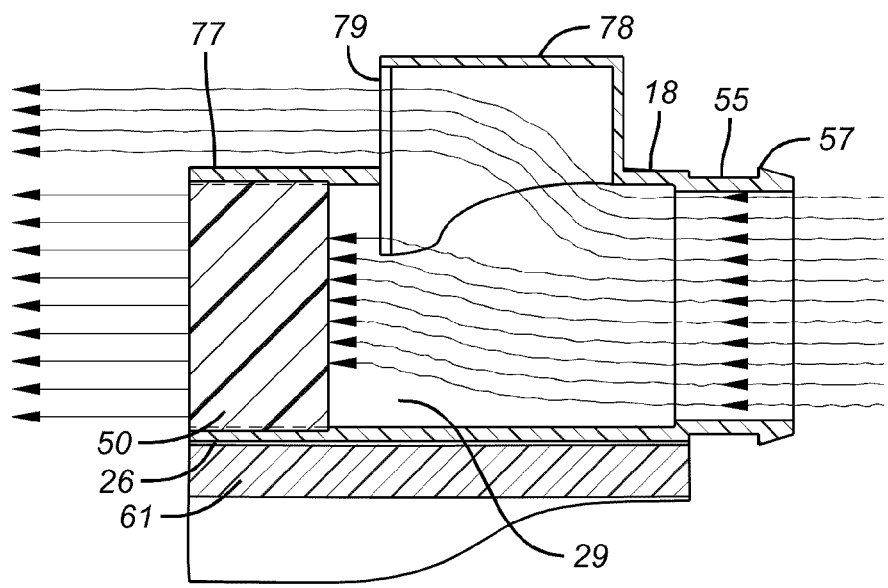
FIG. 8 is a side sectional view of the embodiment of FIG. 7 schematically depicting flow lines of a gas emitted from the emitter assembly

Referring to the embodiments of FIGS. 1-4, housing 28 comprises an upper housing half 16 as best seen in FIG. 3 and a lower housing half 17 as best seen in FIG. 4. Upper housing half 16 has an exterior surface 24 and interior surface 25, and lower housing half 17 has an exterior surface 26 and interior surface 27. Upper housing half 16 is joined to lower housing half 17 to form a housing 28 enclosing chamber 29. In an embodiment, upper housing half 16 widens laterally outwardly from a narrow neck portion 18 to a wide portion 20 that terminates in upper mouth portion 22, and lower housing half 17 widens laterally outwardly from a narrow neck portion 19 to a wide portion 21 that terminates in lower mouth portion 23. The wide portion 20 of upper housing half 16 is generally outwardly curving or convex both in exterior surface 24 and interior surface 25. The wide portion 21 of lower housing half 17 is generally incurvate or inwardly curving both in exterior surface 26 and interior surface 27. The incurvate lower surface 26 of the embodiment depicted is used where the emitter is to be placed on a generally cylindrical or curvate anatomical surface such as a limb adjacent where joint surgery is to be performed. The incurvate shape given outlet 41 allows outlet 41 to be located close to an anatomical curvate surface along the entire length of the outlet, as depicted in FIG. 4.

In the embodiment depicted in FIGS. 3 and 4, flow guides are provided inside emitter assembly 15 between inlet 33 and outlet 41, placed for distributing sterile gas across the surface area of flow conditioning media. In an embodiment, upper housing half 16 has a pair of baffles 30, 31 angled obtusely to one another and spaced apart in front of the upper half 32 of a cylindrical inlet 33 into the chamber 29 formed when upper and lower housing halves 16 and 17 are joined. Similarly, lower housing half 17 has a pair of baffles 34, 35 angled obtusely to one another and spaced apart in front of the lower half 36 of cylindrical inlet 33. The bottom edges 37, 38 of upper baffles 30, 31 engage the top edges 39, 40 of lower baffles 34, 35 when upper and lower housing halves 16 and 17 are joined, to form diverging flow guides 64 (30+34) and 66 (31+35). Upper and lower cylindrical halves, respectively 32 and 36, engage one another to form cylindrical inlet 33, and upper and lower mouth portions, respectively 22 and 23, engage to form outlet 41, when upper and lower housing halves 16 and 17 are joined. Sterile gas entering chamber 29 through inlet 33 is partially admitted straight ahead through a gap 42, 43 between the spaced apart baffle units 64 and 65 and is partially diverted by flow guides 64, 65 laterally outwardly from the central portions of chamber 29.

Upper and lower mouth or outlet portions, respectively 22, 23, terminate in boundary edges, respectively 44, 45, between their exterior surfaces, respectively 24, 26, and their interior surfaces, respectively 25, 27. Between baffles 30, 31 and mouth portion 22 in upper housing half 16 is a raised ridge 46 spanning the width of upper housing half 16. Similarly, between baffles 34, 35 and mouth portion 23 in lower housing half 17 is a raised ridge 47 spanning the width of lower housing half 16. The portion of upper housing half 16 between lip 44 and ridge 46 is an upper land 48. The portion of lower housing half 17 between lip 45 and ridge 47 is a lower land 49. On joinder of upper and lower housing halves 16, 17, upper and lower lands 48, 49 lodge a diffuser (FIGS. 1-2, see also FIGS. 7-8) comprising a porous media 50 within chamber 29 proximate outlet 41 through which sterile gas received in inlet 33 is passed. The purpose of porous media 50 is to ensure that the air exiting outlet 41 is all traveling in the same direction (unidirectional) at the same speed to provide coherent flow from outlet 41 free of turbulence. The media creates a uniform backpressure along its internal surface that allows the air to emerge at a constant velocity along its external surface. Porous media 50 is shaped to fit within and fully occupy the space in the chamber demarked by the upper and lower lands 48, 49 and suitably is a foam diffuser media in the range from 70 to 100 ppi (pores per linear inch), for example 80 ppi, foam filter media at a thickness fitting in lands 48, 49, for example, about 1 inch thick. Alternatively, a finely porous diffuser screen or panel known in the art to produce closely layered laminar flow may be used.

Referring to FIG. 3, upper housing 16 is provided with a pair of slotted outlet ears 51, 52 on opposite lateral sides of the housing proximate outlet 41, and is also provided with a pair of slotted inlet ears 53, 54 on opposite lateral sides of the housing proximate inlet 33. The exterior surface of cylindrical inlet half 32 of upper housing half 16 is formed with a recessed land 55 the distal rim 56 of which tapers distally to form a barb half 57. Similarly, the exterior surface of cylindrical inlet half 36 of lower housing half 17 is formed with a recessed land 58 the distal rim 59 of which tapers distally to form a barb half 60. Joinder of upper housing half 16 to lower housing half 16 provides a circular barb connection 14 for connecting hose 12 to inlet 33.

Referring to FIGS. 1, 2, 6 and 7, a shape conforming barrier 61 is in continuous contact with the lower exterior surface 26 of lower housing half 17 along the width of lower mouth 23 and, perforce, outlet 41, for shape conforming placement of the assembly directly on a portion 102 of the anatomy of a surgical patient adjacent the incision site. "Shape conforming" means that the barrier 61 under the generally shaped incurvate lower housing half 17 accommodates to the size of the specific shape of the anatomical portion of a particular patient, in the range from slim to obese, on which the generally anatomically conforming emitter housing is placed. In an embodiment, the shape conforming barrier is a pad. A conformable pad accommodates various sizes for the same general anatomical shape, prevents particle entrainment of air and particles from underneath the housing 28, and assists in minimizing the distance between the incurvate outlet 41 and the patient. This establishes flow adhering to the surface anatomy of the patient across the site of incision to avoid separation of flow from that surface.

An embodiment of a shape conforming barrier 61 may be a pad of self-conforming material. An example of a self-conforming material is a three-fourths inch thick white ether foam shaped to correspond (FIG. 2) to the shape underside 26 of emitter assembly 15. A pressure sensitive adhesive ("PSA") backing is applied on one side allowing the assembler to peel off a liner to reveal a sticky backing for adhering the foam material to the underside 26 of assembly 15. Self conforming material is compressible but may take a permanent set once deformed to conform to the anatomical surface of the patient, or may be resilient after deformation. An advantage of resilient self-conforming material is that the surgeon may move or shift the emitter during surgery and a resilient self-conforming material will maintain the barrier at the new placement.

Emitter assembly 15 is placed substantially anatomically levelly on the surface of anatomical portion 102 and secured to the anatomically portion to maintain a substantially anatomically level orientation of outlet 41 relative to the surface at the site of the anatomy where the surgery is to occur. Referring to FIGS. 5 and 6, emitter assembly 15 is conformingly applied substantially anatomically levelly to an anatomical surface 102 adjacent surgical site 70. Sterile gas from hose 12 is passed through diffuser 50 of emitter assembly 15 at flow conditions that provide a coherent non-turbulent flow 71 which is adherent at a boundary layer 72 to anatomical surface 102. Barrier 61 prevents ambient air and air particles from being entrained in the flow from underneath emitter assembly 15. The conforming substantially anatomically level application of fluid conditioner assembly 15 creates a flow profile similar to a fluid flowing over a flat surface. As coherent non-turbulent flow moves over the surface 102 in a direction indicated by the flow arrows, viscous forces acting on boundary layer 71 hinder the flow of the adherent boundary layer relative to the higher layers, and the higher layers move at a higher velocity than the lower and boundary layers. Eventually this will cause transition from a coherent non-turbulent flow to a turbulent flow that will separate the boundary layer 71 from surface 102 and cause the flow no longer to adhere to surface 102. Placement of emitter assembly 15 must not be so distant from surgical site 72 as to cause the surgery to be outside the protective layer of sterile coherent non-turbulent gas flowed from emitter assembly 15. Depending on the flow conditions selected, emitter assembly is suitably placed within 3 to 12 inches from the surgery site. Flow conditions for providing a coherent non-turbulent flow from emitter assembly 15 include a relatively moderate flow velocity maintained substantially constant in a range from about 180 to 400 ft/min. In an embodiment, the dimensions of a flow outlet of an emitter suitably is about 8 inches wide and about a 1.9 inches high for a cross sectional area of 0.108 ft$^2$ giving a flow rate of from 19.4 ft$^3$/min to 43.2 ft$^3$/min at a flow velocity of from 180 to 400 ft/min.

At least one releasable fastener is employed for releasably securing emitter assembly 15 to the anatomical portion 102 substantially anatomically levelly in shape conforming contact therewith. In an embodiment, a PSA backing may be applied to both sides of the self conforming material, one backing being used to adhere the material to the underside 26 of assembly 15, and the other backing may be used to adhere the self conforming material to the anatomical portion 102 or a protective sterilized film adhered to anatomical surface 102, in either case, substantially anatomically levelly and in shape conforming contact therewith (FIGS. 5-6). The adhesive is releasable, allowing the assembly to be positioned and repositioned during the course of a surgical procedure.

FIGS. 1-3 illustrate an embodiment especially suited to arthroplasty surgeries, such as hip or knee joint replacement. In this embodiment, the releasable fastener comprises at least one mounting strap and strap fastener affixed to the emitter assembly. In the embodiments of FIGS. 1-3, a male clip end 62 of a strap 63 inserted through slotted ear 51, passed across the exterior surface 24 of upper housing half 16, and inserted though slotted ear 52, is positioned to be passed around an anatomical limb, for example, an upper thigh in the case of hip or knee surgery, and inserted into a female clasp end 66 of the fastener, which is fitted with a release for releasing the male clip end 62. A similar strap arrangement is provided at the inlet end of emitter assembly 15. A male clip end (not seen) of a strap 68 inserted through slotted ear 53, passed across the exterior surface 24 of the neck portion 18 of upper cylindrical half 32, and inserted though slotted ear 54, is positioned to be passed around the anatomical limb and inserted into a female clasp end 69 of the fastener, which is fitted with a release for releasing the male end. Although mounting straps and fasteners have been depicted, any manner of releasable fastening may be used, such as any button, clasp, strap, tie, buckle, zipper, catch, snap, or hook and eye fastener. Placement of the mounting straps at the front and the back of the flow conditioning assembly allows the surgeon to strap the assembly firmly in place. By providing two straps, the assembly can be strapped down evenly, making the outlet flow approximately parallel, and in the case of the incurvate shape tangent, to the patient. Also, the distance between the bottom of the outlet 41 and the patient is further minimized when the straps are tightened, compressing the conformable pad.

In use of the embodiment of FIGS. 1-6, the risk of intrusion of ambient airborne bacteria into a surgery site during surgery is reduced by providing a emitter assembly, such as emitter assembly 15, for direct placement on a portion 102 of a patient's surface anatomy immediately adjacent the surgery site, substantially anatomically level with the anatomical portion 102. Emitter assembly 15 has upper and lower exterior surfaces 24, 26, a chamber 29 within such exterior surfaces, chamber 29 having an inlet 33 adapted to receive sterile gas from hose 12 and an outlet 41 spaced from inlet 33, outlet 41 having a height and width predetermined to establish a height and width of a protective envelope, and porous media 50 within chamber 29 proximate outlet 41 through which sterile gas received in inlet 33 is passed to provide coherent non-turbulent flow from outlet 41. Shape conforming barrier 61 in continuous contact with lower exterior surface 26 of emitter assembly 15 along the width of outlet 41 provides for shape conforming placement of assembly 15 directly on anatomical portion 102 adjacent the surgical site to prevent entrance of ambient gas between the lower exterior surface 26 of assembly 15 and anatomical portion 102. A high efficiency particulate air filter source 11 of sterile gas to inlet 33 is provided. Emitter assembly 15 is secured to anatomical portion 102 immediately adjacent to the surgical site with outlet 41 facing the site substantially anatomically level with anatomical portion 102 and with barrier 61 in shape conforming contact with anatomical portion 102 to prevent entrance of ambient gas between lower exterior surface 26 and anatomical portion 102. Sterile gas is caused to flow from source 11 through inlet 33 into chamber 29, thence through porous media 50 to provide flow coherence, and thence out outlet 41, at a velocity sufficient to form over the surgical site a flow cocoon or envelope 80 of substantially coherent non-turbulent sterile gas having upper flow boundaries 81, lower flow boundaries 82 and lateral flow boundaries 83 shaped by outlet 41. The lower boundaries 81 maintain a boundary layer 84 adjacent the anatomical surface 102 of the patient at least to the surgical site 101 and potentially at least to 0.5 meters distant from the emitter outlet. Lateral boundaries 83 are wider than the surgical site, and upper boundaries 81 have velocities effective to entrain ambient particles impinging on the upper boundaries 81 and sweep them past surgical site 101. In an application of this method, the sterile gas passes from the outlet at a velocity from about 55 to about 122 m/min (about 180 to about 400 ft/min). The sterile gas source 11 is a high efficiency particulate air filter source capable of removing at least 90% of air borne particulates 0.3 micrometers and larger in diameter.

Another embodiment is illustrated in FIG. 7. In this embodiment like elements as for the embodiment of FIGS. 1-6 carry the same reference numerals and need no further description. Although not shown in FIG. 7 to avoid obscuring other details, it is to be understood that internal baffles are present in the embodiment of FIG. 7 as in the embodiment of FIG. 1-6. The upper housing half 75 of emitter assembly 76 of FIG. 7 additionally comprises a raised flat surface 77 on at least a portion of the upper external surface 24 of emitter assembly 76, surface 77 providing a tray useful for placement of surgical instruments. The tray surface suitably supports a rubber or other polymeric friction pad (not shown) providing a high grip surface for the instruments. Between tray surface 77 and upper neck portion 18, upper housing half 75 also has an elevated roof portion 78 that opens in an upper outlet 79 from the interior of emitter assembly 76. Outlet 79 faces and opens onto tray 75 for passing sterile gas across tray 75 to maintain a sterile field on the tray for sterile instruments. As indicated by FIG. 8, the sterile gas flow across tray 77 not only sweeps away any ambient airborne microbes that might otherwise fall onto the instruments, but also passes over the top of the sterile gas flow field emerging from outlet 41 for sweeping any microbes that might be on the instruments if the instruments become non-sterile from usage or if non-sterile when first placed on the tray. There is no flow diffuser such as flow diffuser 50 to condition the sterile gas emerging from upper outlet 79 and while the gas emerging from upper outlet 79 is sterile, passage of the gas over instruments placed in the path of the emergent gas can transition the gas into a turbulent flow, and this is useful, in that any airborne microbes swept from the sterile area over tray 77 are disbursed by the turbulence out away from the operating table while all the time the cocoon zone created by sterile coherent non-turbulent gas emerging from lower outlet 32 protects the surgical site from those and other airborne microbes, Thus there is also provided a method of maintaining sterile surgical instruments sterile, comprising placing the instruments on a tray 77 located on at least a portion of an upper surface of a emitter assembly 76 comprising upper and lower exterior surfaces 15, 17 and a chamber 28 within the exterior surfaces that has an inlet 24 adapted to receive sterile gas from a source, such as through hose 12, and also has a plurality of outlets each spaced from inlet 24 and vertically spaced from one another, a lower outlet 32 having a height and width predetermined to establish a height and width of a cocooning zone, and an upper outlet 79 facing and opening across tray 77. Sterile gas received in inlet 24 is passed through porous media 41 within chamber 28 proximate lower outlet 24 to provide coherent non-turbulent flow from lower outlet 32. A shape conforming barrier 52 is in continuous contact with lower exterior surface 17 along the width of lower outlet 32 for shape conforming placement of assembly 76 directly on a portion of anatomy of a patient adjacent a site for surgical incision in the patient to prevent entrance of ambient gas between lower exterior surface 17 and the portion of anatomy on which the assembly 76 is placed. Sterile gas is flowed over tray 77 from upper outlet 79 while a unidirectional coherent non-turbulent flow field of sterile gas is flowed from lower outlet 32 substantially anatomically levelly along and attached to the anatomical surface of a surgical patient toward the incision site from a position adjacent the incision site. The sterile gas from outlet 32 passes along the anatomy to the incision site under flow conditions sufficient to maintain a boundary layer of the flow field attached to the anatomical surface for a distance extending at least through the surgical site, while entrainment of ambient particles under the flow field is prevented by barrier 61.

Use of the flow conditioning assembly embodiments described in FIGS. 1-4 was tested for its ability to provide a three dimensional zone of substantially coherent non-turbulent gaseous flow layering a site such as one where a surgery would be performed, to protect the site from intrusion of ambient airborne particles during the surgery. The tests are described in Test Examples 1-5.

Test Example 1

Particulate Reduction

Figure 9:
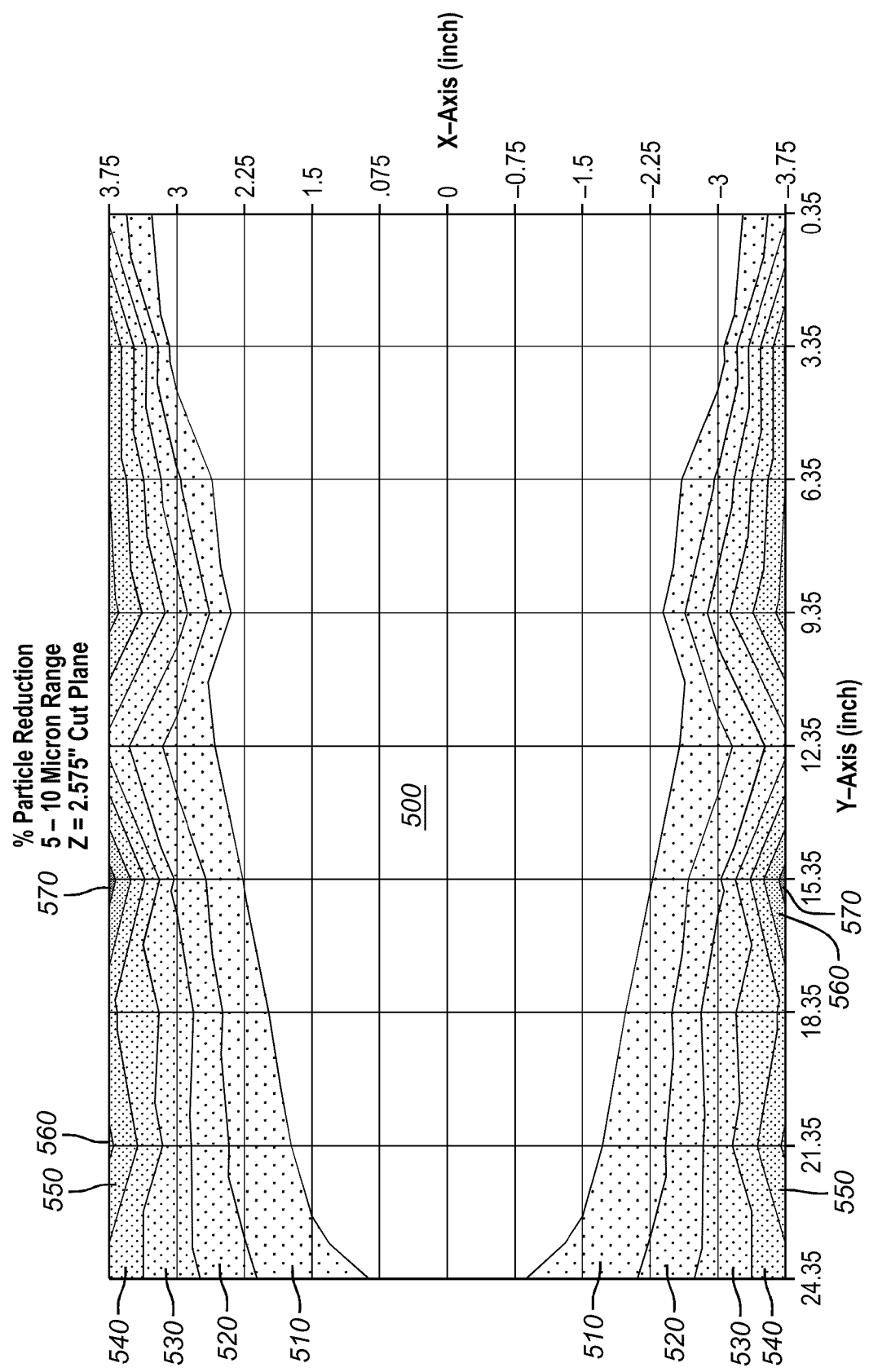
FIG. 9 is a graph showing the results of the test of Test Example 1.

A map of the particulate reductions for X (width) and Y (length) locations was generated using a test fixture. A device system in accordance with the embodiment 10 depicted in FIG. 1 (in this and subsequent examples called the "device") was used to create a clean air envelope on a test surface. Particulate count readings within the clean air envelope at discrete locations were compared to the ambient levels so a percent reduction could be computed. Data was taken over a grid spanning 7.5" wide and 24.35" long, with data taken every 0.75" in the X direction and 3" in the Y direction. A stainless steel tube was used as a probe to sample at various locations while having a minimum impact on the performance of the system. Sterile air was flowed through the device at about 4 ft/sec at a flow rate of about 0.24 ft$^3$/sec. FIG. 9 is a graph of the results, with the device blowing sterile air in the Y-direction, toward the 23.35" mark. Measuring reduction of particulates in sizes 5 µm and greater, reference numerals indicate percent of reduction as follows:

| Reference numeral | Percent reduction |
| --- | --- |
| 500 | 90-100 |
| 510 | 80-90 |
| 520 | 70-80 |
| 530 | 60-70 |
| 540 | 50-60 |
| 550 | 40-50 |
| 560 | 30-40 |
| 570 | 20-30 |

The results show that the device is capable of reducing particulates in sizes 5 µm and greater by 90-100% over an area greater than 5" wide by 20" long. (The reading on the particle counter at 10 µm is all particles 10 µm and greater).

Test Example 2

Substantially Anatomically Level Flow

Figure 10:
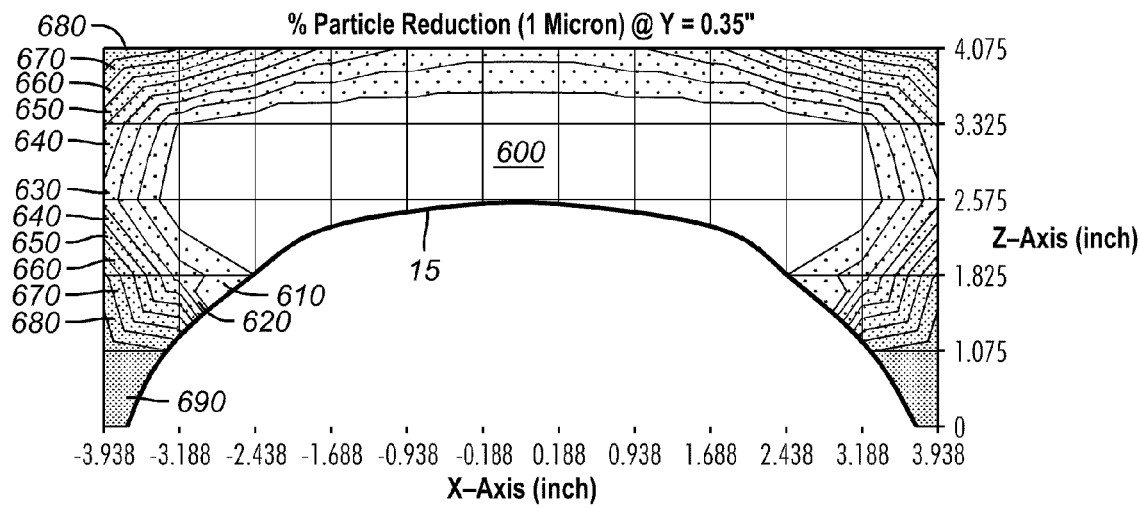
FIGS. 10, 11 and 12 are graphs showing the results of the test of Test Example 2
Figure 11:
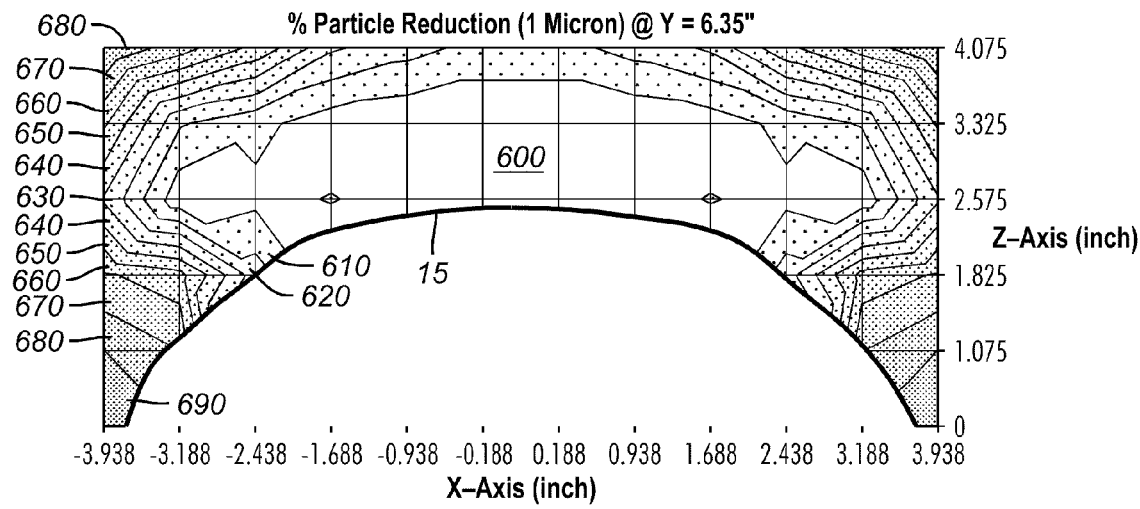
Figure 12:
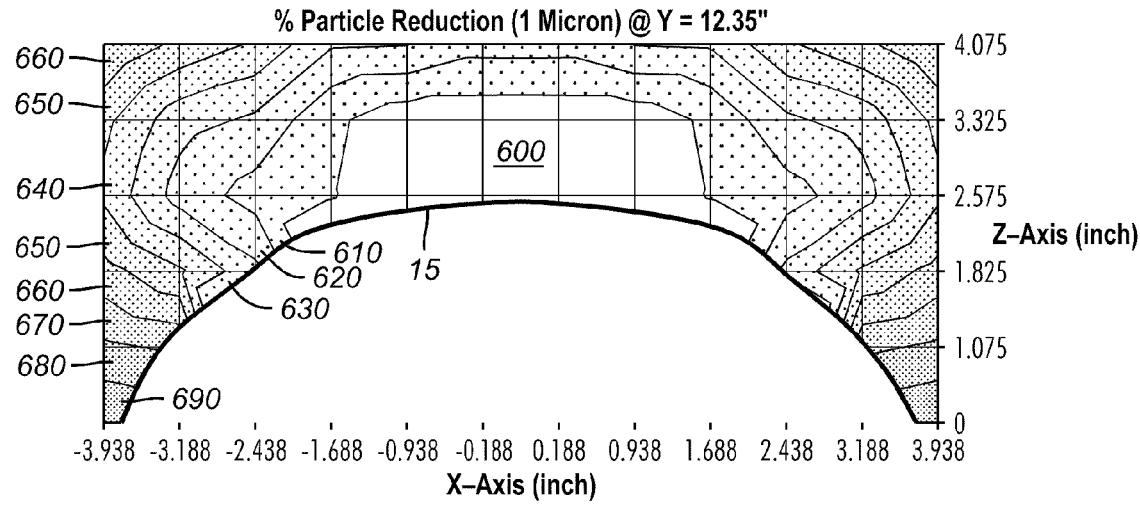

In the embodiments depicted above in which the exterior lower surface of emitter assembly 15 is incurvate, the adherence of flow to the anatomical surface is on a curvate anatomical surface, not a flat surface. The ability of the device to create an envelope of clean air along a curved portion of anatomy was examined by mounting the device onto a convex cylindrical surface with a radius of curvature of 8" and a length of 27". These dimensions were chosen to approximate the dimensions of a human thigh. Cross-sectional maps of the particulate reductions in the X (width)-Z (height) plane were generated by taking measurements, using the methodologies and performance settings of Example 1, along the length of the cylindrical surface. FIGS. 10, 11 and 12 show the particle reduction efficiencies, respectively, at Y distances of 0.35", 6.35", and 12.35" away from the device air emitter. Measuring reduction of particulates in sizes 5 µm and greater, reference numerals indicate percent of reduction as follows

| Reference numeral | Percent reduction |
| --- | --- |
| 600 | 90-100 |
| 610 | 80-90 |
| 620 | 70-80 |
| 630 | 60-70 |
| 640 | 50-60 |
| 650 | 40-50 |
| 660 | 30-40 |
| 670 | 20-30 |
| 680 | 10-20 |
| 690 | 0-10 |

The maps indicate that the clean air zone adheres and conforms to the curved test surface.

Test Example 3

Bacterial Reduction Ambient Air

Figure 13:
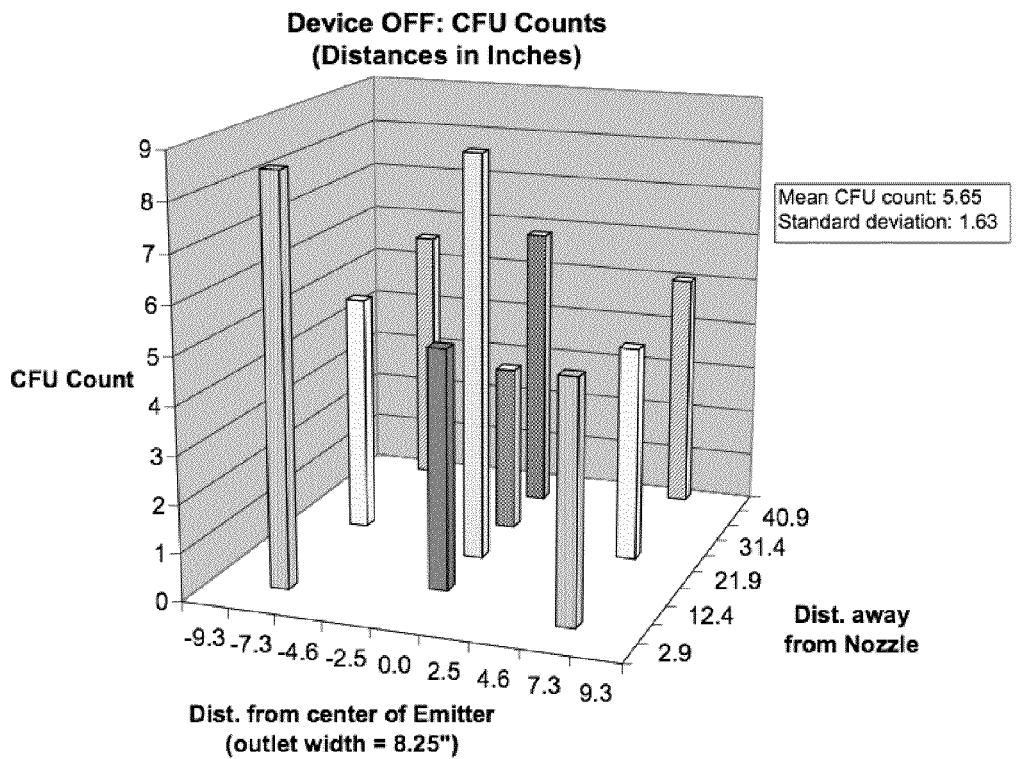
FIGS. 13 and 14 are graphs showing the results of the test of Test Example 3.
Figure 14:
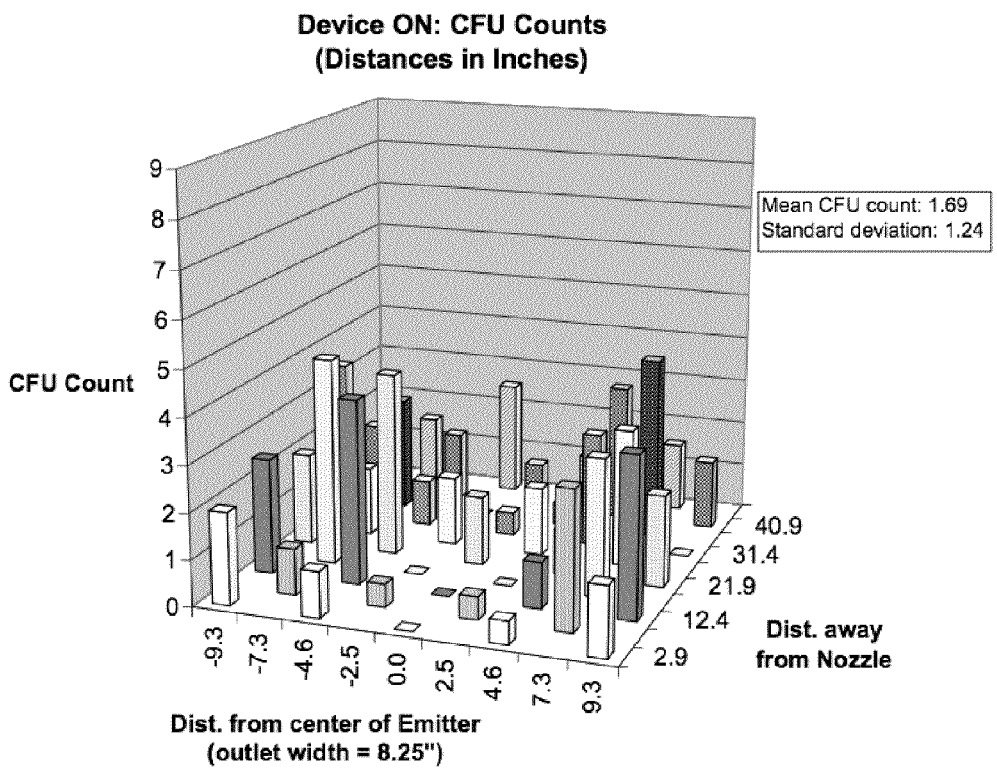

Numerous 10 cm diameter settle plates (tryptic soy agar with 5% sheep's blood) were exposed over a 24" wide by 48" long surface to ambient air conditions. The device outlet was placed adjacent to the surface to examine its area of effect. The plates, which are 1.5 cm tall, were set onto a flat surface in order to mimic the potential effect of physical structures to disrupt the coherent non-turbulent flow field. During a control set of trials, 10 settle plates were exposed to ambient air for 30 minutes with the device in place but not activated ("Device OFF"). During an experimental set of trials, 45 plates were exposed to ambient air for 30 minutes with the device activated ("Device ON"). For settle plates exposed during the Device OFF control runs, the mean bacterial colony forming unit ("CFU") count was 5.65, standard deviation of 1.63 (FIG. 13). For the experiment group (Device ON), the mean CFU count on plates exposed during the experiment runs was 1.69, standard deviation of 1.24, with the bacteria populations heavily weighted to areas outside the width of the device and furthest away (FIG. 14). An area approximately 6" wide and 17" long directly proximate to the outlet of the device showed near-zero CFU readings. A typical incision during hip arthroplasty, which is approximately 5 inches square or smaller, would fit within the boundary area. These data also indicate that the device does not concentrate airborne bacteria and redistribute them downstream from the device, which could be an issue if sterile equipment such as surgical implants and instrumentation were placed in that area.

Test Example 4

Bacterial Reduction Challenge

Challenge test trials were conducted during which a high concentration of airborne bacteria, representing approximately 24 times the normal level of ambient airborne bacteria, was introduced over an area approximately 10" wide by 27" long that was being protected by the device. Thirty-five (35) settle plates (65 mm diameter, tryptic soy agar, 5% sheep's blood) were evenly spaced throughout the test surface and were exposed to the challenge conditions for 10 minutes during each trial. Measuring reduction of particulates in sizes 5 µm and greater, reference numerals indicate percent of reduction as follows:

| Reference numeral | Percent reduction |
|---|---|
| 700 | 90-100 |
| 710 | 80-90 |
| 720 | 70-80 |
| 730 | 60-70 |
| 740 | 50-60 |
| 750 | 40-50 |
| 760 | 30-40 |
| 770 | 20-30 |
| 780 | 10-20 |

Figure 15:
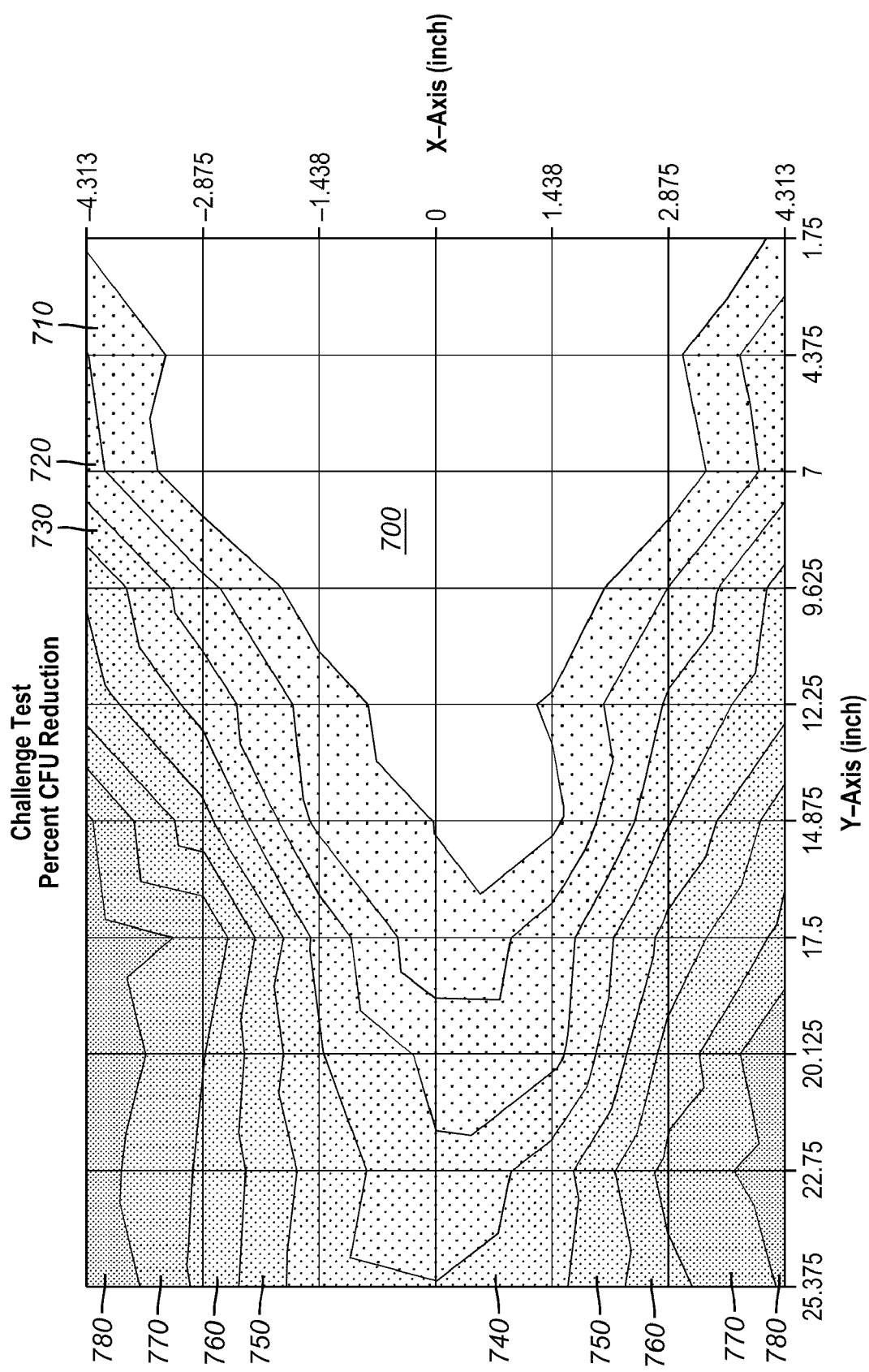
FIG. 15 is a graph showing the results of the test of Test Example 4.

The plate CFU counts demonstrated, as shown in FIG. 15, that the device is capable of reducing the presence of airborne microorganisms by more than 90% in an area greater than approximately 6" wide and 10" long during these extreme conditions.

Test Example 5

Simulated Surgeries Particulate Counts

Figure 16:
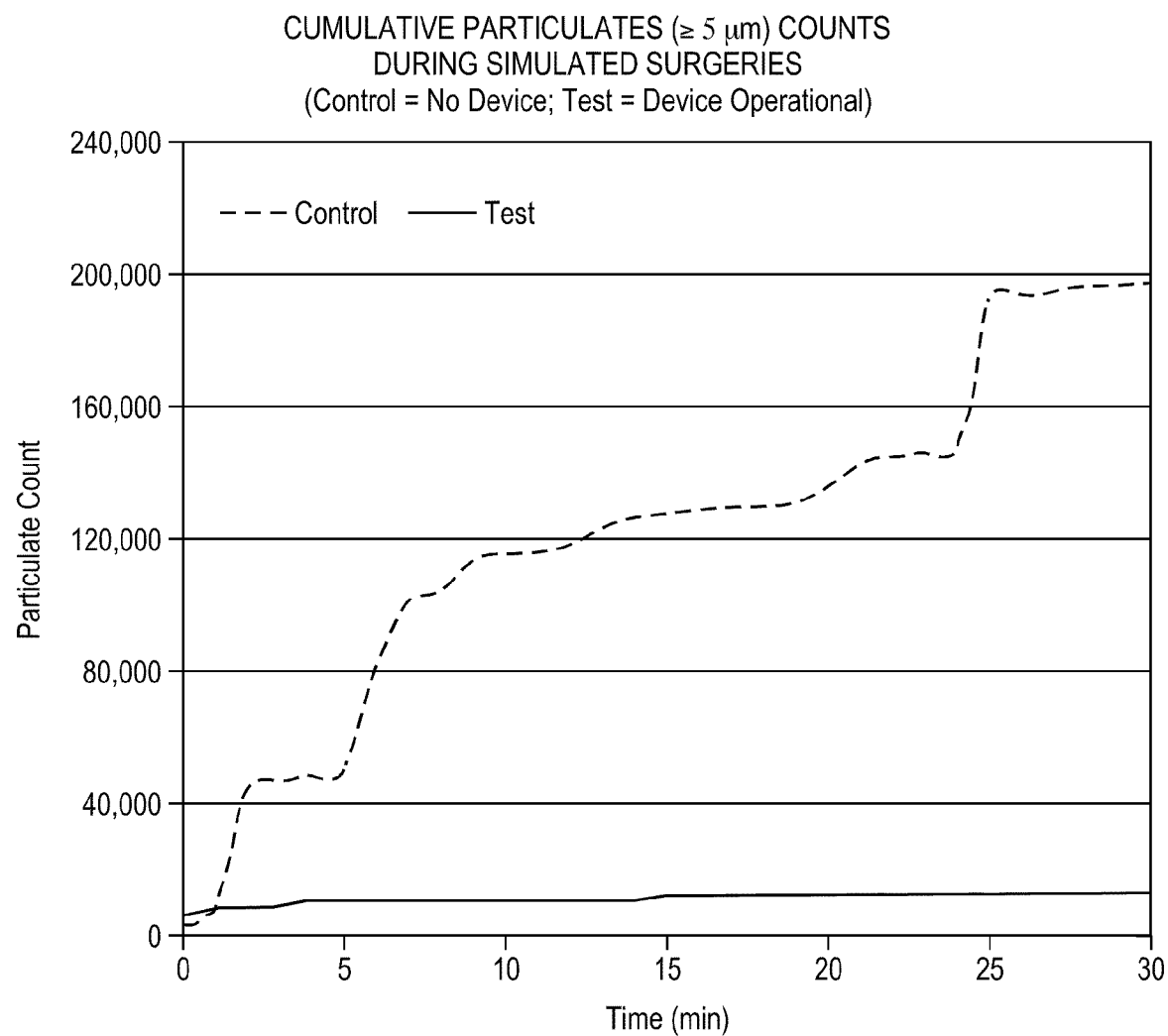
FIG. 16 is a graph showing the results of the test of Test Example 5.

Several total hip arthroplasty surgeries were conducted at an orthopedic hospital on fresh frozen (i.e., not embalmed) cadavers to determine the efficacy of the device when deployed under surgical conditions. The surgeries were conducted using the standard methods, personnel, instruments, and techniques performed by the surgeon except that prosthetic components were not implanted and no anesthesia was administered. All other sterile preparation, instruments, incisions, and methods were representative of an actual surgical procedure. Airborne microbes and particulates were captured through 130 cm lengths of sterile tubing at two locations: within 5 cm of the surgical site under the air envelope provided by the embodiment of FIGS. 1-4 ("Test") and at a location within the sterile field but not under the air envelope ("Control"). In-wound bacteria counts were sampled just prior to closing using the tetrazolium stained membrane imprint (TSMI) method by pressing 47 mm cellulose acetate and nitrate filter membranes onto the wound surface for 20 seconds and transferring them to agar plates. The results of the simulated total hip arthroplasty surgeries in cadavers in which the device was either used (Test) or not used (Control) showed a dramatic reduction in particulate counts at the surgical site throughout the duration of the simulated procedure (see FIG. 16). The average particulate was reduced by 93% in the Test condition (median=36, $95^{th}$ percentile=1960) versus the Control condition (median=1683, $95^{th}$ percentile=35,000).

Flow Simulations

The following Flow Simulation Examples refer to drawings that are black line tracings of computer screen shot color graphics resulting from computer simulations explained in the Flow Simulation Examples. The computer program rendering the simulations employs graphics that use a color spectrum to indicate flow line velocities, gradations from dark to lighter blues to dark to lighter greens to light to darker yellows to light to darker oranges to light to darker reds indicating velocities that increase with movement up the color spectrum, dark blue indicating the slowest velocity and dark red indicating the fastest. Sterile gas emitted from the emitter has velocity and in color the computer graphics of the simulation program display this in the warm colors according to emergent velocity and velocity degradation with distance from point of discharge from the emitter, in some instances moving into the greens. By contrast, ambient air is essentially stationary until given velocity as it is drawn forward by the flow discharged from the emitter, and in color the computer graphics show this in gradations in cool colors (from dark to lighter blues to dark to lighter greens). In the black line drawings of FIGS. 19-34, the lines are black line tracings of the computer screen shots, including the flow lines, and lacking color, several conventions are employed to distinguish the flow lines and their velocities. Flow lines of sterile gas discharged from the outlet of an emitter are shown in solid lines. Weight of a solid line is used to represent velocity, lighter weights indicating a lesser velocity. Flow lines from ambient air are shown as dashed lines. Length of a dash signifies velocity, lesser velocities being indicated by smaller lengths of dash. Reference numerals in the series from 130 to 139 are used to supplement the weighted solid and dash length line conventions. These reference numerals indicate velocities as explained in more detail below. As an aid to assist distinguishing numbers 130-139 representing velocities from other numbers, reference numerals 130-139 are presented in a serif font (Times New Roman) whereas the normal numbers are presented in a san serif font (Arial).

The line drawing tracings illustrate the concepts involved in using an anatomical shape conforming emitter to apply a unidirectional coherent non-turbulent flow field of essentially sterile gas substantially anatomically levelly onto a surface mimicking an anatomical surface of a patient, and illustrate emitters and flows not in conformity with concepts of the invention. Flow Simulation Examples 1 and 2 show simulations of flow using prior art devices. Flow Simulation Example 3 shows an anatomically shape conforming emitter having outlet dimensions substantially the same as in the embodiments of FIGS. 1-4 with the emitter placed anatomically levelly on an emulated anatomical surface, and accords with the present invention. Flow Simulation Examples 4 and 5 demonstrate that even using an emitter having an orifice outlet profile as in Flow Simulation Example 3, the concepts of our invention are not applied because the embodiment either is not anatomically level with the surface (Flow Simulation Example 4) or is not anatomically shape conforming (Flow Simulation Example 5). Flow Simulation Example 6 shows another example of an emitter that is not anatomically shape conforming and does not produce a flow that is anatomically level. As will be seen from these simulations, only Flow Simulation Example 3 provides an essentially sterile unidirectional coherent non-turbulent gas flow field.

Flow Simulation Example 1

Prior Art—Flow Not Horizontally Level with the Surface and Not Sterile

Figure 17:
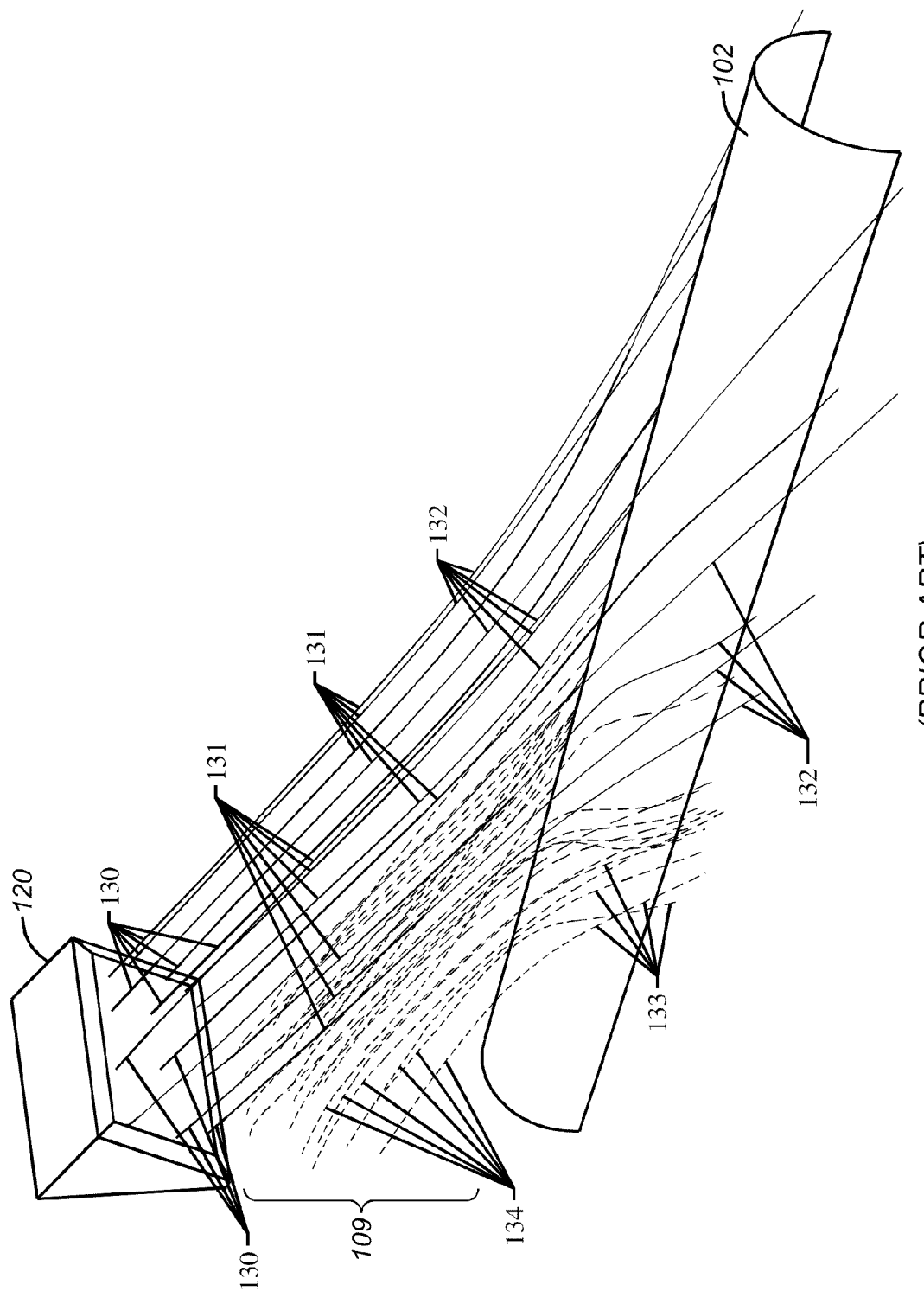
FIG. 17 is an isometric depiction of the flow trace elements emerging from a prior art emitter and passing over an arcuate surface.
Figure 18:
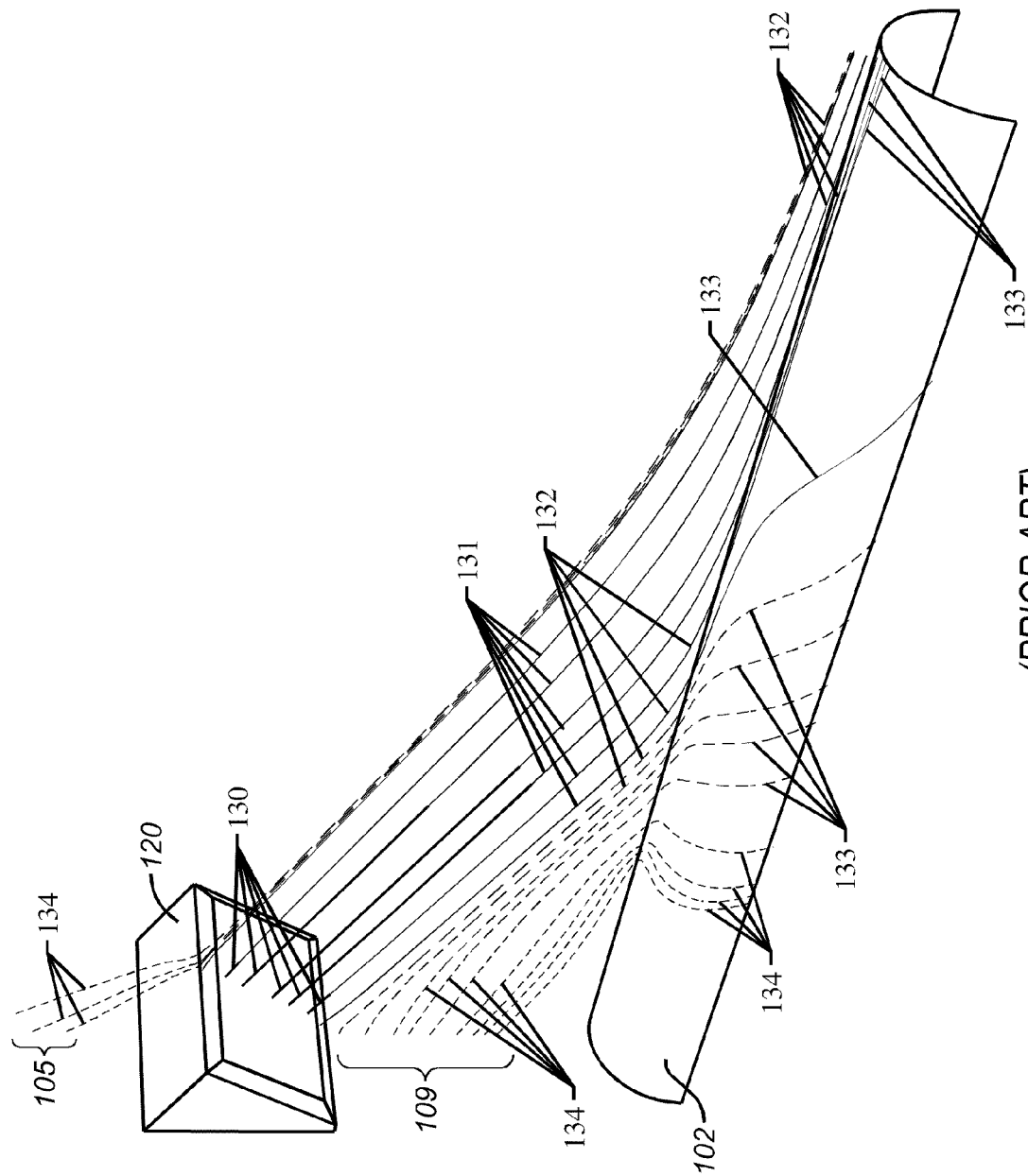
FIG. 18 is a depiction of the flow trace elements in a vertical plane through the center of the emitter of FIG. 17.
Figure 19:
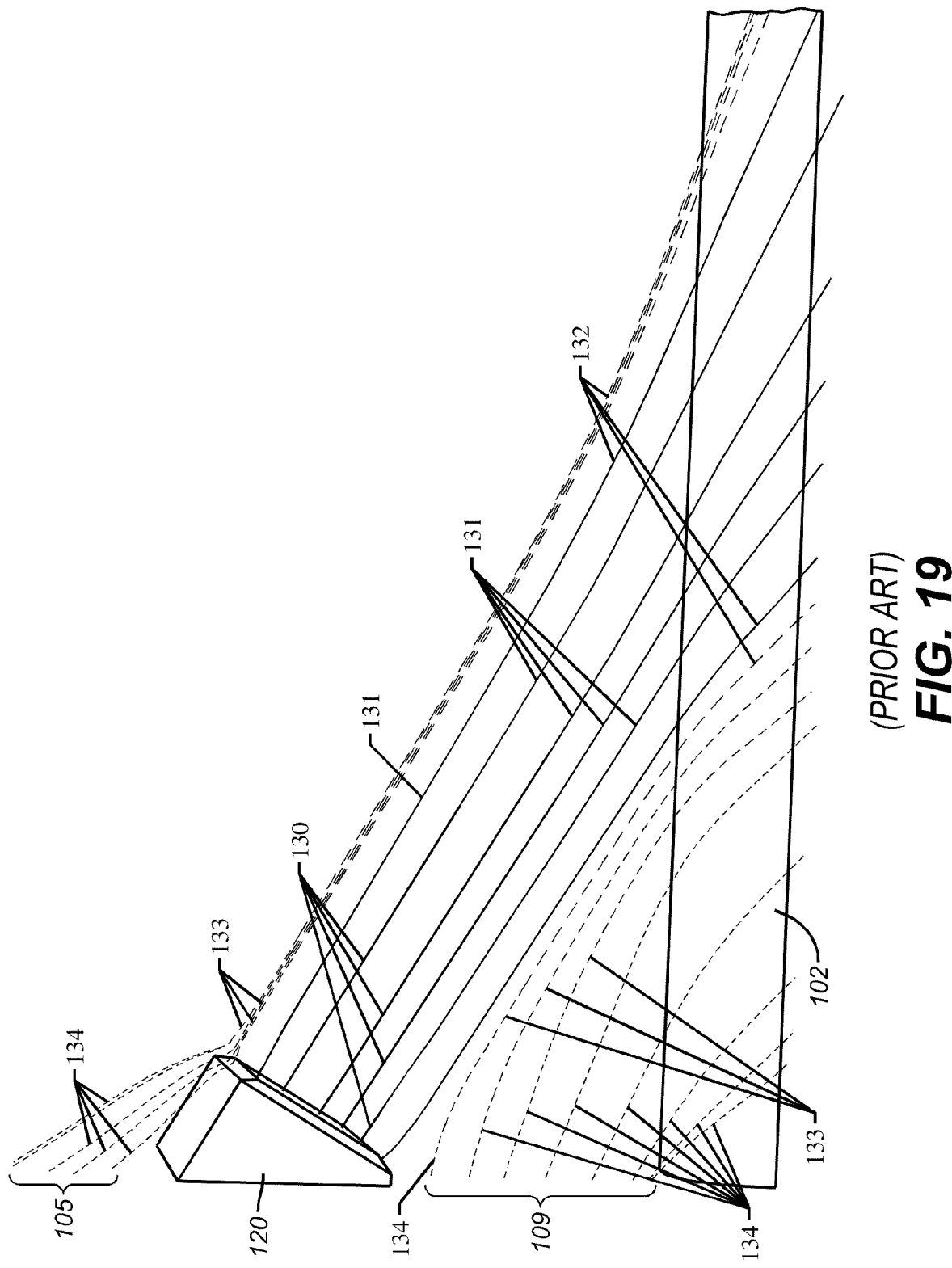
FIG. 19 is a depiction of the flow trace elements at the lateral edge of the emitter of FIG. 17.

Referring to FIGS. 17-19, a series of flow simulations are depicted that employ an emitter configuration of the type described in the article by Thore M, et al.: *Further bacteriological evaluation of the TOUL mobile system delivering ultra-clean air over surgical patients and instruments*, JOURNAL OF HOSPITAL INFECTION 63, 185-192 (2006), noted above as similar to U.S. Pat. No. 3,820,536, configured and deployed as described in that article and employing flow velocities described in that article. The emitter outlet size is 0.55 meters (21.654 inches) wide, 0.4 meters (13.638 inches) high and has a central airflow zone with a peripheral airflow zone 1.5 inches inset from the edges of the emitter. The peripheral zone is angled outwardly 25 degrees. The emitter is 0.681 meters (24.350 inches) above surface 102 and is inclined toward surface 102 at a 60-degree angle. The arcuate surface 102 is an arcuate surface of a segment of a circular horizontally disposed column 14.610 inches in diameter in emulation of an anatomical surface of a surgical patient, such as a thigh. The length of the segment is 10.651 inches. The simulations were performed using a computer program "CFDesign" version 9.0 available from Upfront CFD run on an Intel based PC computer using a Windows XP 64 bit operating system. The following parameters were used for the program simulations: exiting velocity for the central airflow zone was 0.5 m/sec (100 ft/min) and for the peripheral zone was 0.3 m/sec (59 ft/min); a "wall" condition was set on the curved surface; and all other boundaries received P=0 (atmospheric) conditions. Mesh size was: 50 inches wide, 60 inches tall and 100 inches long. The simulation contained 359,866 fluid elements and converged after 325 iterations.

FIG. 17 is an isometric depiction of the flow trace elements (solid lines) emerging from the emitter outlet 120 and passing over surface 102 and also shows flow trace elements for ambient air (dashed lines) drawn into the area and given velocity by the fast flow discharged from the emitter outlet. FIG. 18 depicts the flow trace elements in a vertical plane through the center of the emitter 102. FIG. 19 depicts the flow trace elements at an edge of emitter 120 closest to the viewer. The emitter of FIGS. 17-19 is not anatomically shape conforming and the simulated flow is not "level" and is not "anatomically level" with surface 102. As illustrated by FIGS. 17-19, flow from the emitter 120 (solid lines) is not horizontally level with surface 102, is scattered along surface 102, and large amounts of ambient air 109 (dashed lines) are drawn into the flow under the emitter onto surface 102. This drawn-under ambient air would contaminate sterile gas emitted from emitter 120. Ambient air 105 at the top of emitter 120 is drawn into the airflow and swept forward, increasing in speed.

Reference numerals 130-134 supplement the convention of weighted solid and dashed lines for illustrating velocities. Solid flow lines at velocity 130 have a heavier weight than solid flow lines at a velocity of 131; solid flow lines at a velocity of 131 have a heavier weight than solid flow lines at a velocity of 132; solid flow lines at a velocity of 132 have a heavier weight than solid flow lines at a velocity of 133; and solid flow lines at a velocity of 133 have a heavier weight than solid flow lines at a velocity of 134. As mentioned, faster ambient flow lines have longer dash lengths. The same reference numeral is used for a given range of velocities whether the lead to the reference numeral is to a solid line or a dashed line. Nominal ranges of velocities for solid and dashed lines are indicated by reference numbers as follows:

| Reference numeral | Velocity (ft/min.) |
|---|---|
| 130 | from about 80 to about 100 |
| 131 | from about 60 to about 80 |
| 132 | from about 40 to about 60 |
| 133 | from about 30 to about 40 |
| 134 | from about 5 to about 30 |

Flow lines having more than one reference number along their length indicate changing velocities along that length.

Flow Simulation Examples 2-6

Introductory Comments

In Flow Simulation Examples 2-6 and corresponding FIGS. 20-34, the flow simulations used the same nominal emitter flow velocity (350 ft/min), so a higher series 135-139 of reference numerals indicative of higher flow velocities are employed in FIGS. 20-34 to supplement the convention of weighted solid lines and dashed lines for illustrating velocities. Nominal ranges of velocities for solid and dashed lines are indicated in FIGS. 20-34 by reference numbers as follows:

| Reference numeral | Velocity (ft/min.) |
|---|---|
| 135 | from about 280 to about 350 |
| 136 | from about 220 to about 280 |
| 137 | from about 140 to about 220 |
| 138 | from about 80 to about 140 |
| 139 | from about 20 to about 80 |

The same reference numeral is used for a given range of velocities whether the reference numeral leads to a solid line or a dashed line. Solid flow lines at a velocity of 135 have a heavier weight than solid flow lines at a velocity of 136, solid flow lines at a velocity of 136 have a heavier weight than solid flow lines at a velocity of 137, and solid flow lines at a velocity of 137 have a heavier weight than solid flow lines at a velocity of 138, and faster ambient flow lines have longer dash lengths. Flow lines having more than one reference number indicate different flow velocities along the length of the flow line.

Flow Simulation Example 2

Prior Art—Coanda Jet Effect, Flow Horizontal But Not Sterile

Figure 20:
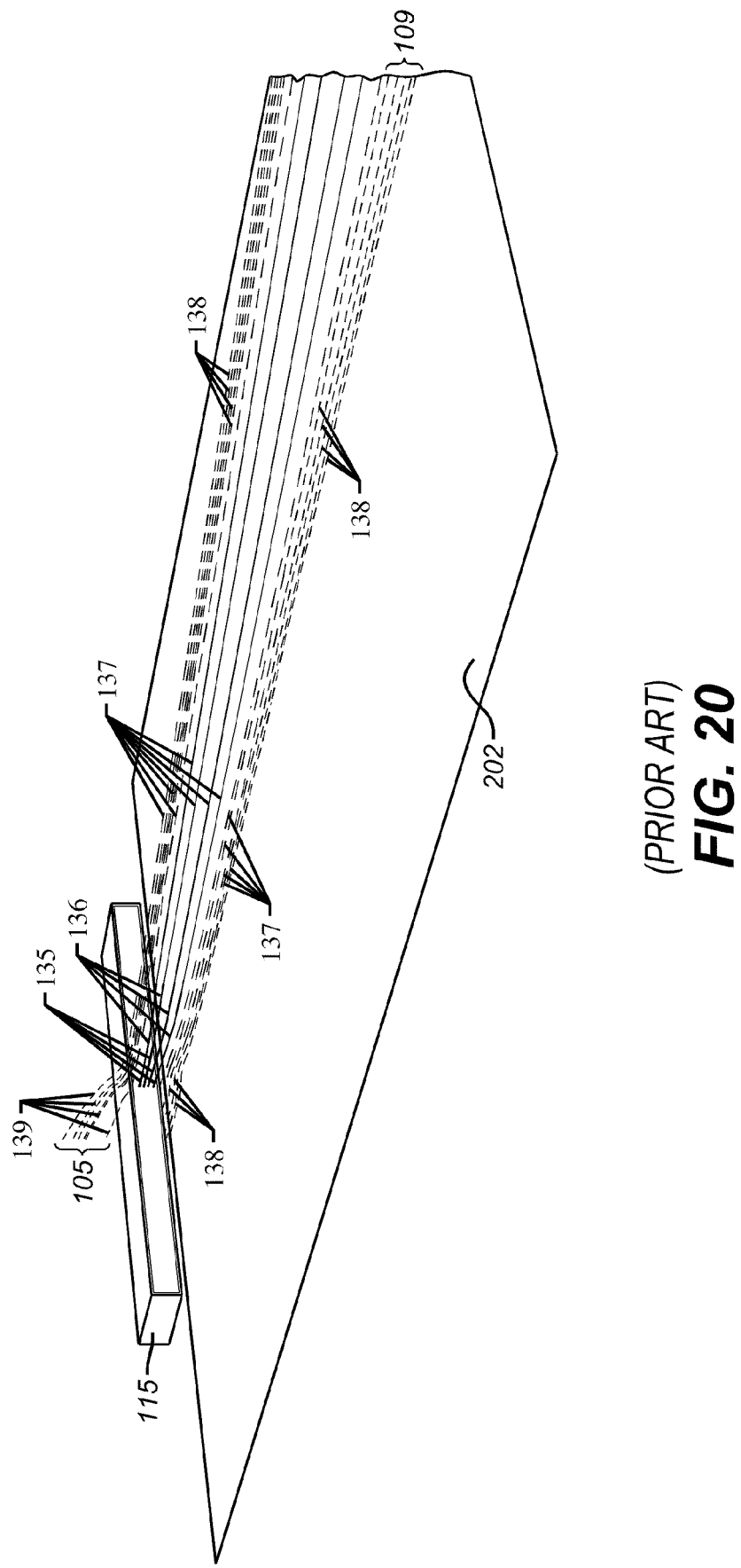
FIG. 20 is an isometric depiction of the flow trace elements emerging from a prior art emitter and passing over a flat surface.

Referring to FIGS. 20-22, a series of flow simulations are depicted that employ a rectilinear flat bottomed emitter 115 that is 8 inches wide and 0.5 inches high (the dimensions of the flat nozzles depicted in U.S. Pat. No. 4,275,719 to Mayer, mentioned above) over a flat plate 202, as in a Coanda Effect for a jet emitted adjacent a flat surface. A space of 0.375 above the flat plate was necessary for simulation stability. The simulations were performed using the same computer program as in Flow Simulation Example 1. The following parameters were used for the program simulations: velocity condition at emitter outlet (exiting emitter) was 350 ft/min; all other boundaries received P=0 (atmospheric) conditions. Mesh size was 16" wide, 12" tall and 24" long. The simulation contained 190,490 fluid elements and converged after 904 iterations FIG. 20 is an isometric depiction of the flow trace elements emerging from the center vertical plane of the outlet of flat emitter 115 and passing over surface 202. FIG. 21 depicts a side view of the flow trace elements in the vertical plane through the center of emitter 115, and FIG. 22 depicts the flow trace elements at the lateral edge of emitter 115 closest to the viewer. As illustrated by FIGS. 20-22, flow from emitter 115 is generally horizontal but is underlain by large amounts of ambient air 109 drawn under emitter 115 and forming part of the flow closest to surface 202, contaminating the flow from emitter 115. As in Flow Simulation Example 1, ambient air 105 at the top of emitter 120 is drawn into the airflow from the emitter and swept forward. Ambient air 107 from the lateral side of emitter 115 is also drawn into the flow and swept forward.

Flow Simulation Example 3

Figure 23:
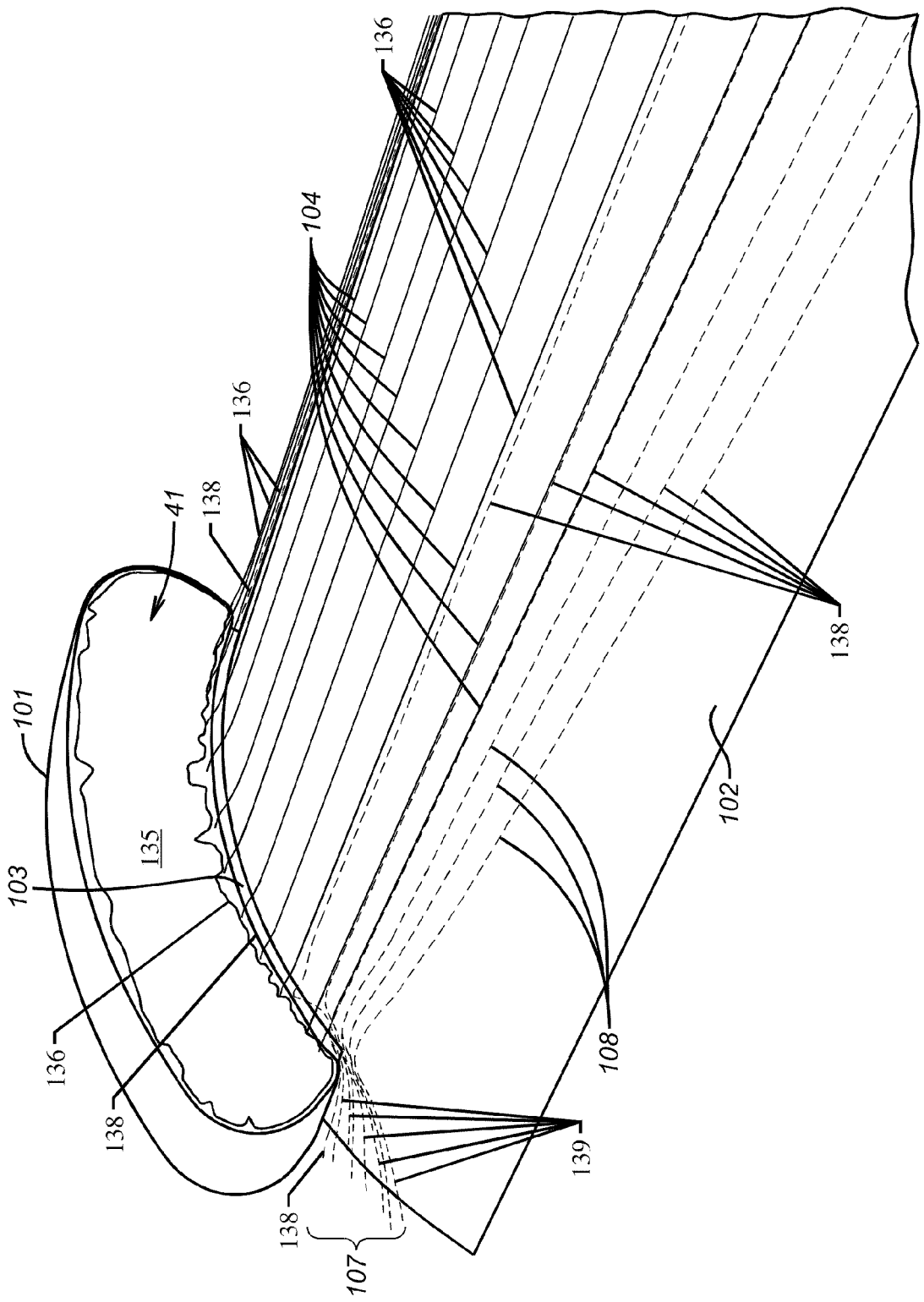
FIG. 23 is an isometric depiction of the flow trace elements emerging from an emitter like emitter assembly of FIGS. 1-4 and passing over an arcuate surface.
Figure 24:
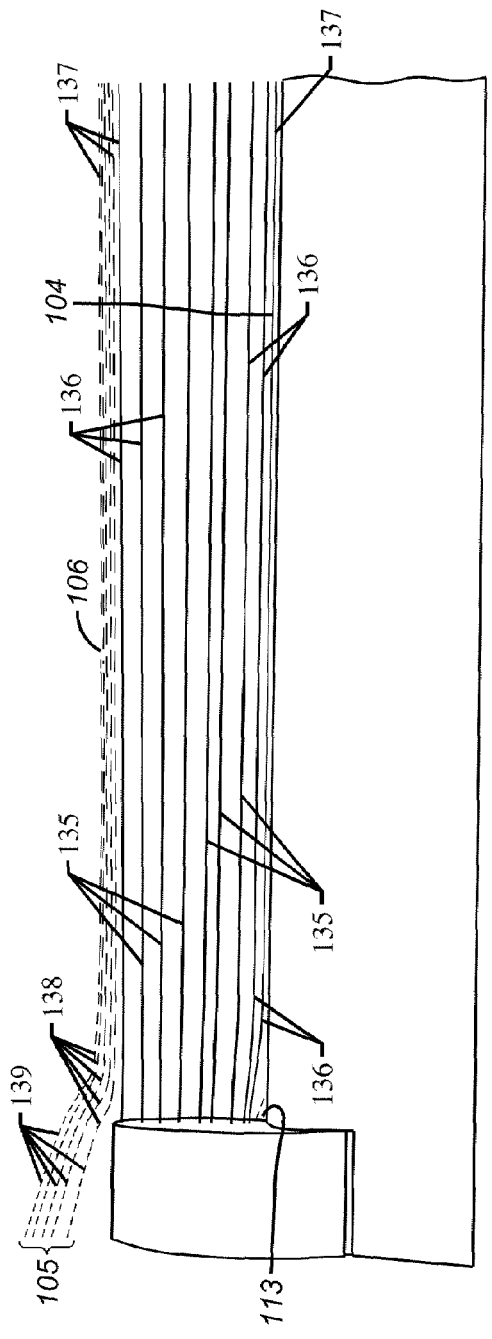
FIG. 24 is a depiction of the flow trace elements in a vertical plane through the center of the emitter of FIG. 23.
Figure 25:
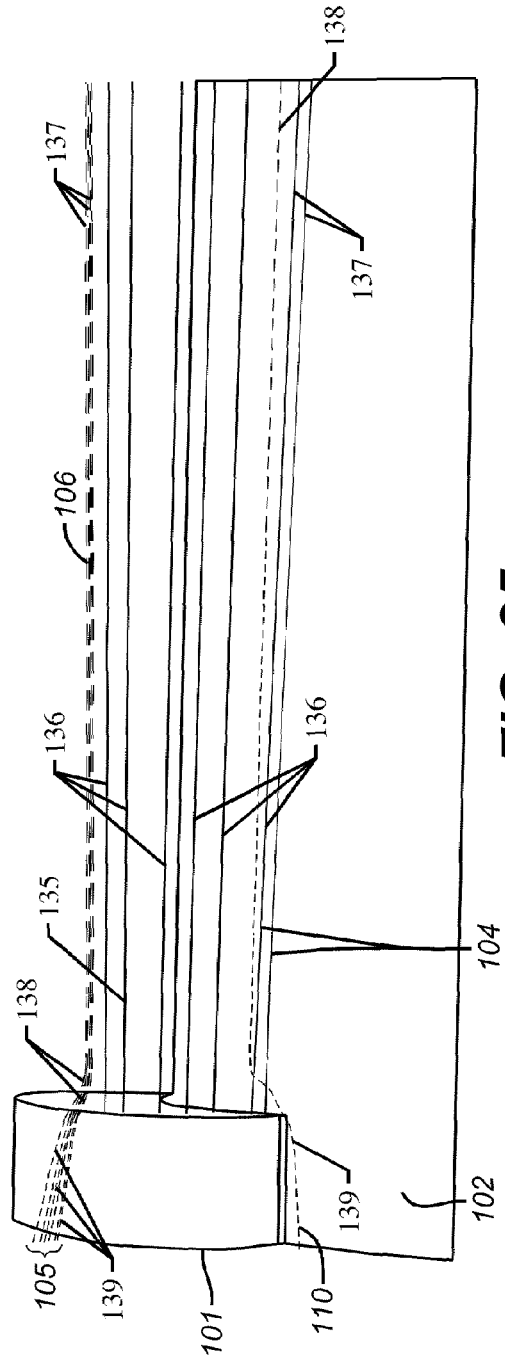
FIG. 25 is a depiction of the flow trace elements at the lateral edge of the emitter of FIG. 23.

Emitter is Anatomically Shape Conforming and Flow is Anatomically Level and Essentially Sterile Referring to FIGS. 23-25, a series of flow simulations are depicted that illustrate the performance characteristics represented by embodiments of the invention used in accordance with the concepts of the invention. FIGS. 23-25 depict traces of flow elements using an anatomically shape conforming emitter a detailed construction of which is described in connection with FIGS. 1-4. The flow simulation in FIGS. 23-25 is one in which the emitter 101 is substantially anatomically level with a surface 102, which for illustration, is an arcuate surface of a segment of a circular horizontally disposed column, as in Flow Simulation Example 1. The emitter 101 conforms to the shape of surface 102, has a width of 8.355 inches and center height of 1.890 inches. It has a surface conformable barrier 103 under the emitter undersurface that is 0.125 inches thick. The arcuate surface is a segment of a circular column 14.610 inches in diameter. The length of the segment is 10.651 inches. The simulations were performed using the same computer program as in Flow Simulation Examples 1 and 2. The following parameters were used for the program simulations: velocity condition at emitter outlet (exiting emitter): 350 ft/min; a "wall" condition on curved surface; all other boundaries received P=0 (atmospheric) conditions; mesh size: 16" wide, 12" tall and 24" long, containing 169,016 fluid elements. The simulation converged after 339 iterations.

FIG. 23 is an isometric depiction of the flow trace elements emerging from the lowest arc of the emitter outlet 41 and passing along surface 102. Reference numeral 135 indicates the exit velocity of flow lines in the boundary band indicated by reference numeral 136, and reference numeral 138 indicates the velocities of flow discharging from the band indicated by 138 at the edge of outlet 41. Flow velocities near the edge of outlet 41 in outer band 138 and next nearest band 136 have less velocity in the interior region 135 of outlet 41. FIG. 24 depicts the flow trace elements exiting in a vertical plane through the center of emitter 101. FIG. 25 depicts the flow trace elements at an edge of emitter 101 closest to the viewer. As illustrated by FIGS. 23-25, flow from the emitter 101 is unidirectional, coherent and non-turbulent, has a boundary layer attached to the surface 102, e.g. at 104, and blocked by barrier 103, no airflow enters the flow field underneath emitter 101, i.e., between the emitter 101 and surface 102. FIGS. 24 and 25 show that ambient air 105 at the top of emitter 101 is entrained and swept along the top edges 106 of the flow field. FIGS. 23 and 25 show that ambient air 107 outside the lateral sides of emitter 101 is entrained as at 108 along the lateral peripheries of the flow field. FIGS. 23-25 show that the 0.125 inch compressed thickness of barrier 103 between the lower margin of the outlet of emitter 101 and surface 102 allows a tiny low pressure area 113 to develop immediately adjacent the lower edge of emitter 101 behind where the lowest flow elements for a boundary layer attach to surface 102, and a trace 110 of ambient air is drawn into low pressure area 113 and is entrained in the flow field. This trace 110 is considered comparatively de minimus compared to the massive amounts of ambient air drawn into the flow immediately over the surface 102 in the prior art (Flow Simulation Examples 1-2) and in Flow Simulation Examples 4-6 that do not conform to the concepts of the invention, and as de minimus thus not contaminating the sterile quality of gas flowed from the emitter to the extent it is no longer essentially sterile.

Flow Simulation Example 4

Figure 26:
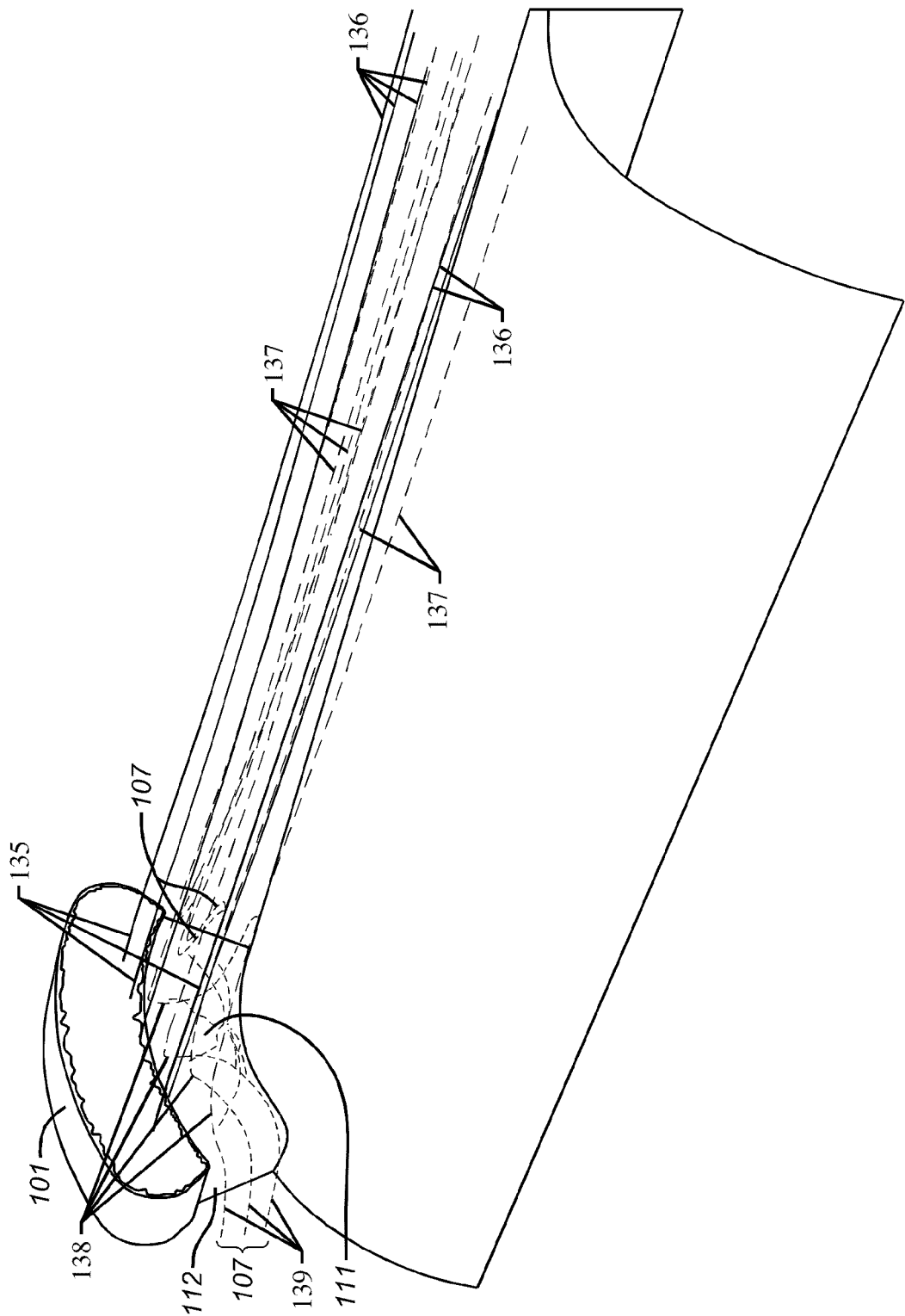
FIG. 26 is an isometric depiction of the flow trace elements emerging from an emitter like emitter assembly of FIGS. 23-25 but having a thicker barrier.
Figure 27:
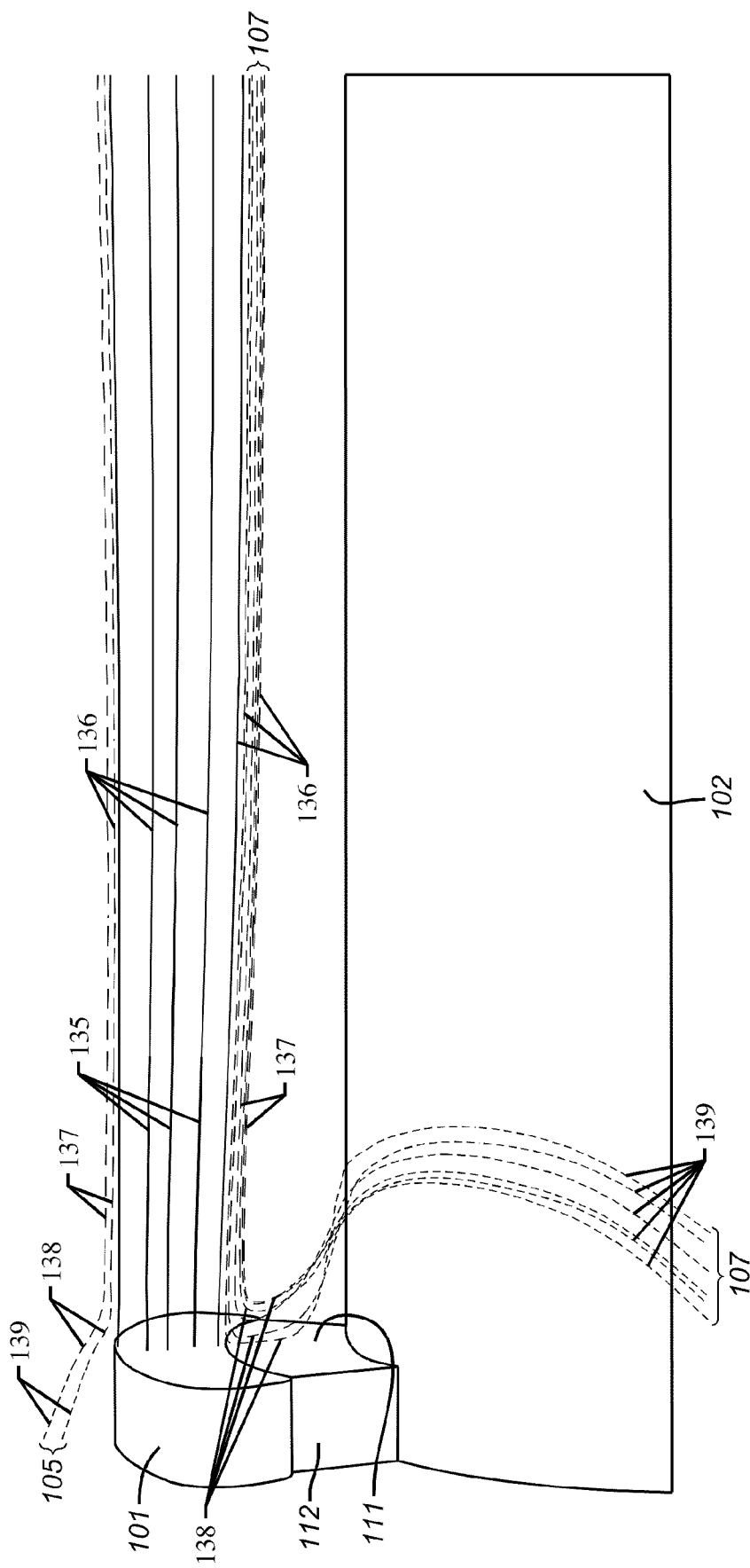
FIG. 27 is a depiction of the flow trace elements in a vertical plane through the center of the emitter of FIG. 26.
Figure 28:
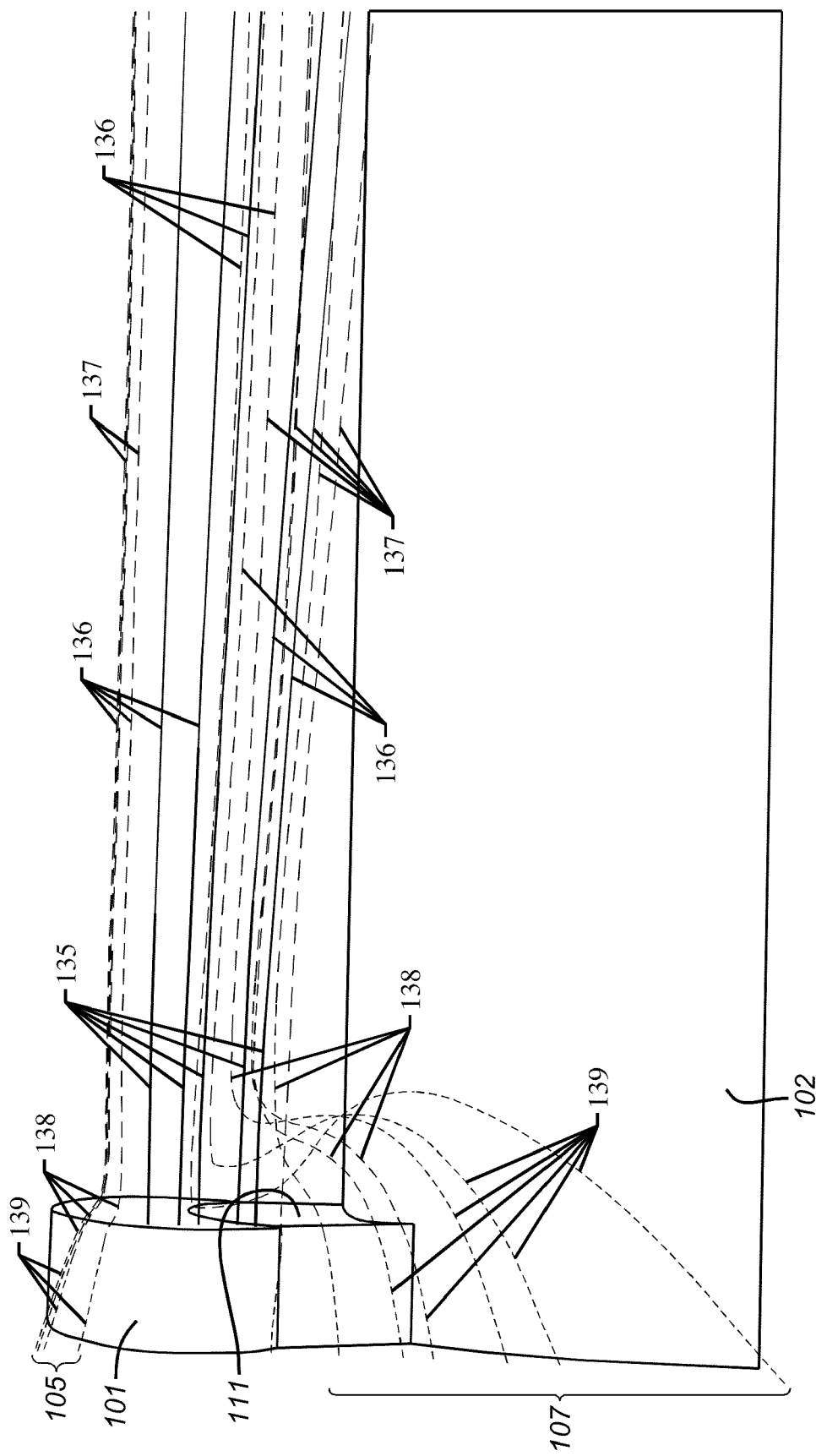
FIG. 28 is a depiction of the flow trace elements at the lateral edge of the emitter of FIG. 26.

Emitter is Anatomically Shape Conforming and Flow is Horizontal But Emitter is Not Anatomically Level with the Surface so Flow is Not Essentially Sterile Referring to FIGS. 26-28, a series of flow simulations are depicted that employ an emitter 101 of the same outlet configuration and dimensions as in FIGS. 1-4, but employing a thicker barrier 112 that is 2 inches thick. The arcuate surface has the same configuration and dimensions as in the Flow Simulation Example 1 and 3. The simulations were performed using the same computer program as in Flow Simulation Example 1-3. The same parameters were used for the program simulations as used in Flow Simulation Example 3, except that the simulation contained 169,016 fluid elements. The simulation converged after 309 iterations.

FIG. 26 is an isometric depiction of the flow trace elements emerging from the bottom of the emitter outlet and passing over surface 102. FIG. 27 depicts the flow trace elements in a vertical plane through the center of emitter 101, and FIG. 28 depicts the flow trace elements at the lateral edge of emitter 101 closest to the viewer. As illustrated by FIGS. 26-28, flow from the emitter 101 is unidirectional, coherent and non-turbulent, and because of barrier 112 no airflow enters the flow field underneath emitter 101, but the flow from emitter 101 is not attached to the surface 102. Emitter 101 is level in the sense of that it is not inclined toward surface 102, and flow is at least initially generally parallel with surface 102, but the lowest part of the gas flow field from the emitter is not level with the surface 102 in the sense that it is sufficiently higher than the anatomical surface that the gas flow does not attach to and form a boundary level with surface 102. Thus although emitter 101 is an anatomically shape conforming emitter, that is, the lower margin of the outlet conforms to the cross sectional contour of surface 102, as does barrier 112, the emitter is not substantially anatomically level with surface 102.

As in FIGS. 24 and 25, in FIGS. 27 and 28 ambient air 105 at the top of emitter 101 is entrained and swept along the top edges of the flow field, but unlike in Flow Simulation Example 3, the lower margin of the outlet of emitter 101 is so high over the surface 102 that the flow from emitter 101 develops a large low pressure area 111 under the outlet, drawing substantial amounts of ambient air 107 turbulently into the interior of the flow field, as shown in FIGS. 26-28. The substantial amounts of ambient air 107 drawn into the flow field are swept over surface 102 beneath the flow field, and would contaminate a surgical field with particulates carried in ambient air, in contrast to the de minimus trace line in Flow Simulation Example 3.

Flow Simulation Example 5

Emitter is Not Anatomically Shape Conforming So Flow is Not Essentially Sterile

Figure 29:
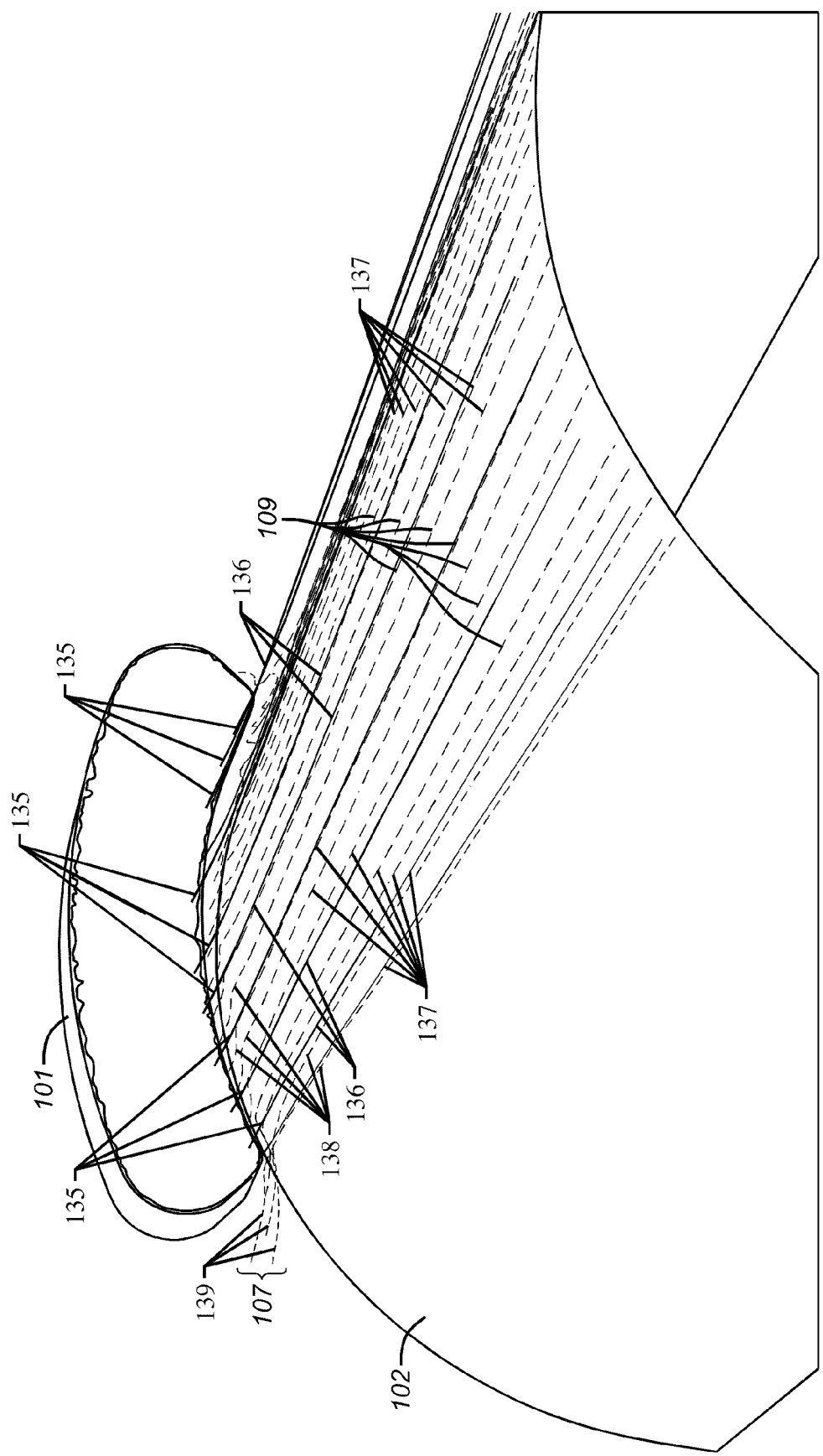
FIG. 29 is an isometric depiction of the flow trace elements emerging from an emitter like emitter assembly of FIG. 23 having no barrier under the emitter, and passing over an arcuate surface.
Figure 30:
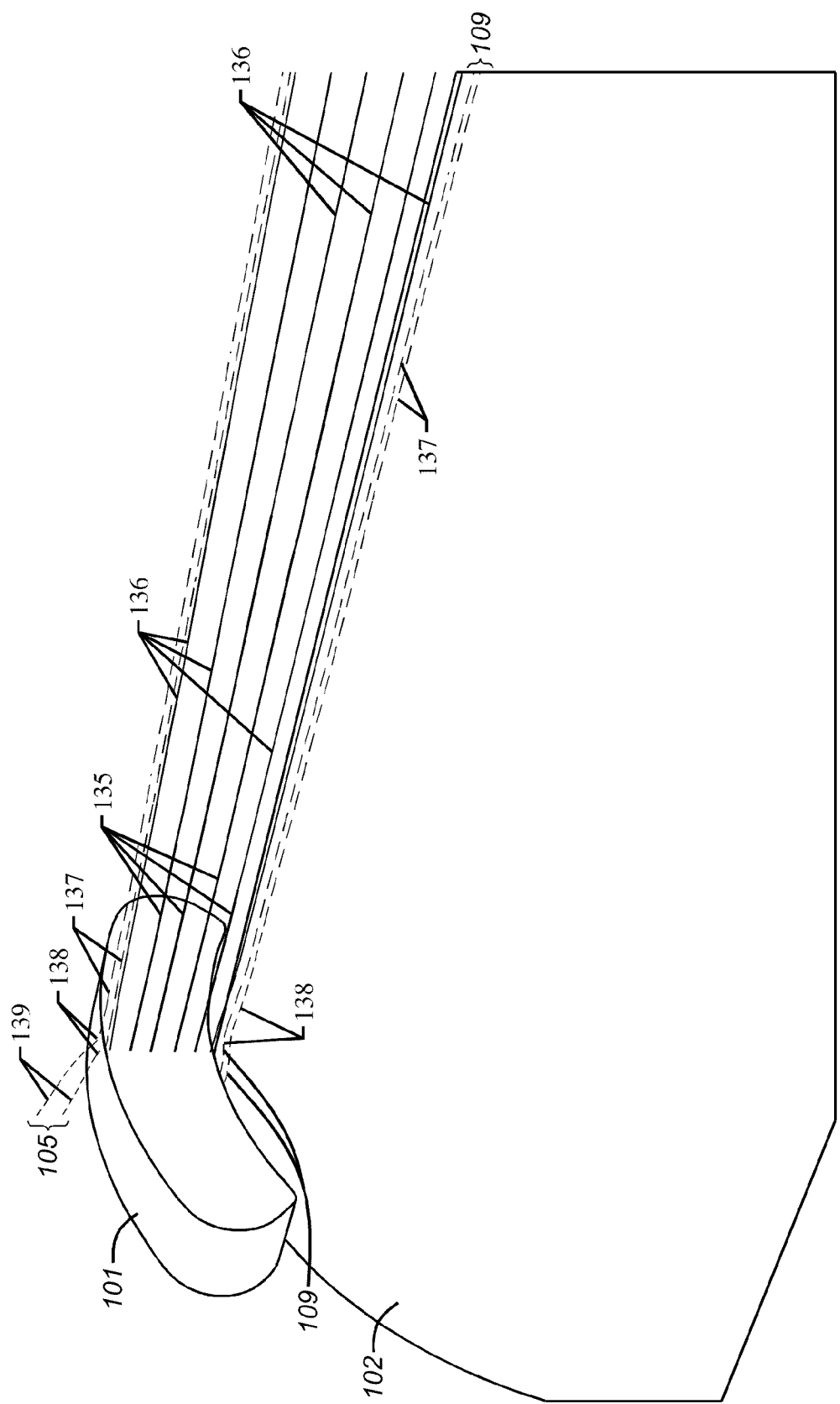
FIG. 30 is a depiction of the flow trace elements in a vertical plane through the center of the emitter of FIG. 29.
Figure 31:
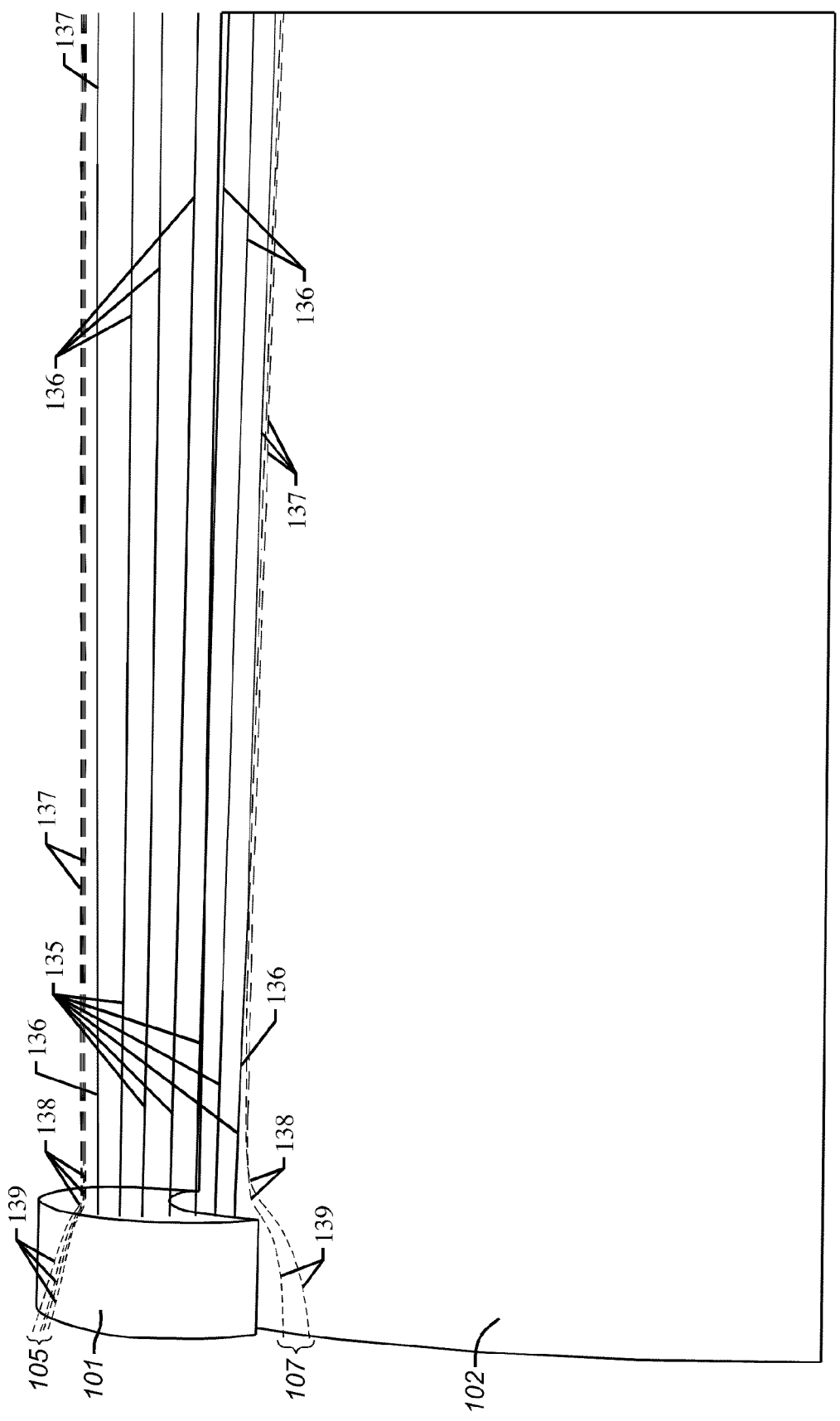
FIG. 31 is a depiction of the flow trace elements at the lateral edge of the emitter of FIG. 29.

Referring to FIGS. 29-31, a series of flow simulations are depicted that employ the same emitter 101 as in FIGS. 23-25, but without the barrier 103 filling a space between the emitter and surface 102. A space of 0.375 was necessary for simulation stability. Arcuate surface 102 has the same configuration and dimensions as in the Flow Simulation Example 3. The simulations were performed using the same computer program as in Flow Simulation Example 3. The same parameters were used for the program simulations as used in Flow Simulation Example 3, except that the simulation contained 161,004 fluid elements. The simulation converged after 259 iterations.

FIG. 29 is an isometric depiction of the flow trace elements emerging from a vertical plane in the center of the emitter outlet and passing over surface 102. FIG. 30 depicts a side view of the flow trace elements in a vertical plane through the center of emitter 101, and FIG. 31 depicts the flow trace elements at the lateral edge of emitter 101 closest to the viewer. As illustrated by FIGS. 29-31, flow from the emitter 101 is unidirectional, coherent and non-turbulent, but because no barrier exists blocking flow under emitter 101, ambient airflow 109 enters underneath emitter 101 and contaminates the flow field, just as it did for Flow Simulation Examples 1 and 2. Because the barrier 103 present in the emitter of Flow Simulation Example 3 is lacking, there is no undersurface so matching the shape of the anatomy where the emitter body is to be affixed and ambient airflow is not substantially completely prevented from penetrating underneath the emitter and as shown it does infiltrate under the emitter and enter the interior of the coherent non-turbulent flow emergent from the emitter outlet. Accordingly the emitter in this Flow Simulation Example 5 is not anatomically shape conforming. FIGS. 29 and 30 are especially clear in showing that ambient air drawn into the emitted flow field contributes largely to the flow that forms a boundary layer on the surface, so the flow over the surface is not essentially sterile.

Flow Simulation Example 6

Figure 32:
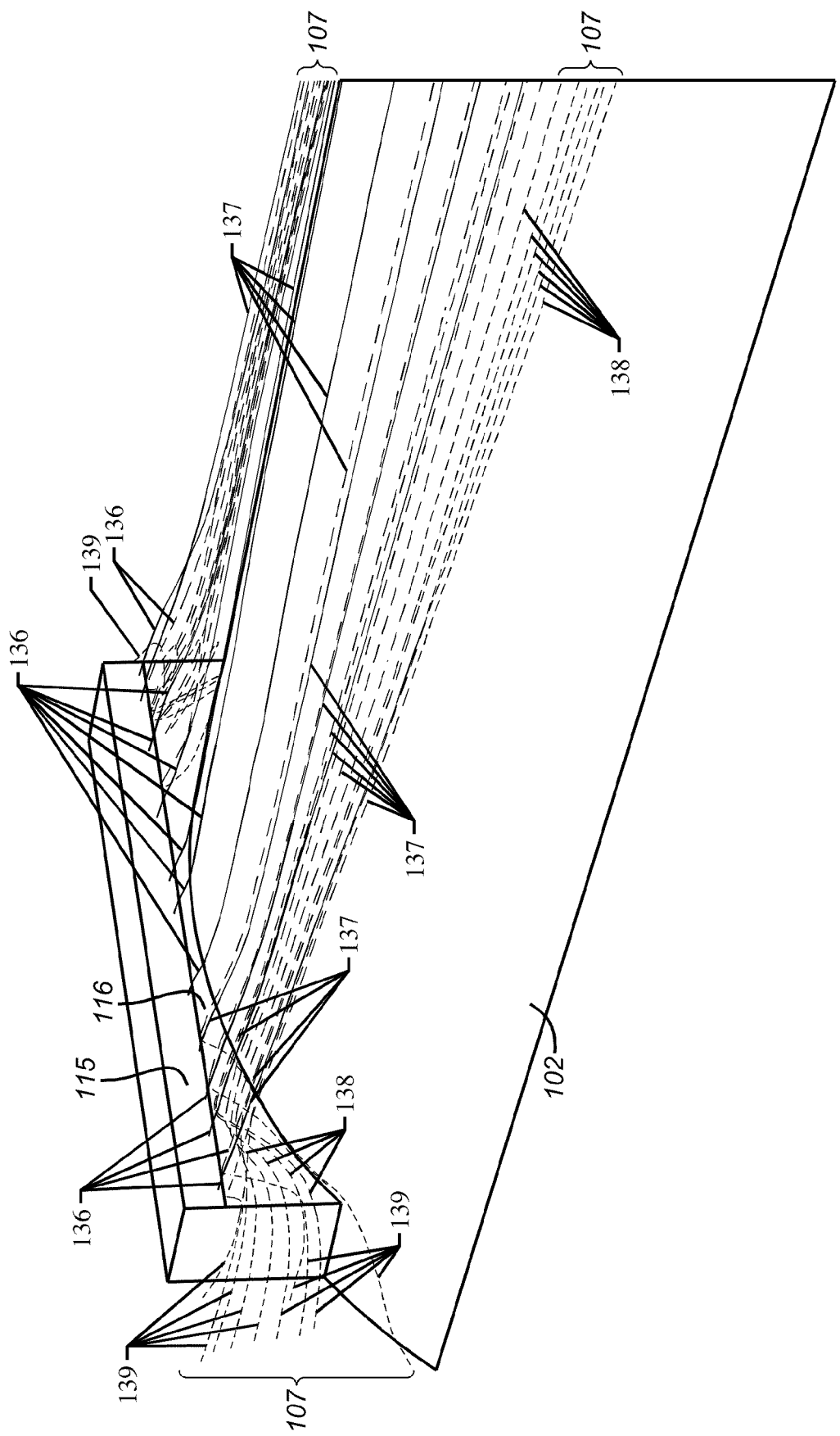
FIG. 32 is a isometric depiction of the flow trace elements emerging from a modified emitter of the type shown in FIG. 20 and passing over an arcuate surface.

Emitter is Not Anatomically Shape Conforming
Flow is Not Anatomically Level and Not Sterile Referring to FIGS. 32-34, a series of flow simulations are depicted that employ the same emitter shape and dimensions as in Flow Simulation Example 2 but over an arcuate surface as in Flow Simulation Examples 1, 3, 4 and 5, and further, unlike in Flow Simulation Example 2, the emitter is additionally supplied with a barrier 116 that substantially conforms to surface 102. However the lower edge or margin of the outlet of emitter 115 is not anatomically level with surface 102 over the width of the outlet. The lower margin of the outlet of emitter 115 is "level" with surface 102 only at the point of tangency at the apex of arcuate surface 102. The barrier 116 has the same compressed thickness where the outlet of emitter 115 is level at that tangent point as in Flow Simulation Example 3 but the barrier increases in thickness on both sides of the point of tangency. The arcuate surface has the same configuration and dimensions as in the Flow Simulation Examples 1, 3, 4 and 5. The simulations were performed using the same computer program as in all the other Flow Simulation Examples. While the shape and dimensions of the emitter are different, the other parameters are the same as used for the program simulations in Flow Simulation Examples 1 and 2, except that the simulation contained 161,004 fluid elements. The simulation converged after 259 iterations.

FIG. 32 is an isometric depiction of the flow trace elements emerging from the bottom of the outlet of flat emitter 115 and passing over surface 102. FIG. 33 depicts the flow trace elements in a vertical plane through the center of emitter 115, and FIG. 34 depicts the flow trace elements at the lateral edge of emitter 115 closest to the viewer. As illustrated by FIGS. 32-34, flow from emitter 115 is unidirectional and generally horizontal, and because of barrier 116 no airflow enters the flow field underneath emitter 115, but the sterile flow from emitter 115 is attached to the surface 102 only in a vertical longitudinal plane perpendicular to the point of tangency of the surface 102. On either side of the vertical plane the sterile flow is increasingly not attached to surface 102, because the lower margin or boundary of the orifice or outlet of the emitter 115 is not essentially uniformly along its width equidistant to the undersurface of the emitter (barrier 116) coming into contact with surface 102. Thus although emitter 115 is has an anatomically shape conforming barrier 116, because the lower margin or boundary of the orifice or outlet of the emitter is not essentially uniformly along its width equidistant to the undersurface of the emitter (barrier 116) coming into contact with surface 102, emitter 115 is not an anatomically shape conforming emitter, as a consequence of which the flow is not substantially anatomically level with surface 102.

FIGS. 33 and 34 also show, as in FIGS. 21 and 22, that ambient air 105 at the top of emitter 115 is entrained and swept along the top edges of the flow field, but unlike in Flow Simulation Example 2, the height of the lower margin of the outlet of emitter 115 over the surface 102 on either side of the point of tangency at which the emitter is placed causes the flow to develop a substantial low pressure area on both such sides under the outlet that draws large amounts of ambient air 107 into the flow field, as especially shown in FIGS. 33 and 34. Because the flow field is not attached to the surface where the low-pressure area develops, the substantial amounts of ambient air 107 drawn into the flow field are swept over surface 102 beneath the flow field, and would contaminate a surgical field with particulates carried in ambient air.

CONCLUSION

We have described embodiments and methods to create a localized dynamic flow field of coherent non-turbulent sterile gas, approximately 0.5 meters (approximately 20 inches) long, directly on and over a surgical site to protect the site from intrusion of ambient airborne particles. The embodiments and methods place an emitter of sterile gas on the anatomical surface of a patient adjacent the site of the surgical incision substantially anatomically level with the anatomy at that site. The emitter is constructed to match the general anatomical surface of the patient adjacent the incision site, to adapt to the particular size of that anatomical surface, and to prevent entrainment of air and airborne particles beneath the emitter. The emitter emits a unidirectional coherent non-turbulent flow of sterile gas, which "hugs" the patient in the localized field and surrounds the surgical site. By locating this protective shield directly on the patient at the surgical site, the shield is placed under the surgical staff leaning over the incision and overhanging operating room equipment with the result that surgical staff, operating room equipment and others in the operating room are placed "outside" the protective shield. It is shown that this very effectively reduces the presence of airborne particulate and bacteria within the surgical shield. Additionally the localized flow field becomes turbulent past the area of shield, with the result that particles riding the peripheries of the field are dispersed by the turbulence away from the surgical table and sterilized equipment out into the operating room rather than remaining concentrated in a coherent flow passing over the sterilized equipment.

The above disclosed subject matter is to be considered illustrative, and not restrictive, and the appended claims are intended to cover all modifications, enhancements, and other embodiments that fall within the true scope of the present invention, which to the maximum extent allowed by law, is to be determined by the broadest permissible interpretation of the following claims and their equivalents, unrestricted or limited by the foregoing detailed descriptions of embodiments of the invention.

The invention claimed is:

1. Apparatus for protecting a site of surgical incision in the anatomy of a patient from ambient airborne microbes in an operating room in which the site is exposed to the operating room atmosphere during surgery, comprising an anatomically shape conformable emitter configured (a) to emit sterile coherent non-turbulent gas, in one direction only, into ambient air in the operating room, substantially anatomically levelly with the anatomical surface of the patient adjacent only one side of said site for flow of the emitted sterile coherent non-turbulent gas substantially anatomically levelly across the site unidirectionally from said one side of site to an opposite side thereof, and (b) to block entry of ambient air under said emitter into said flow.

2. The apparatus of claim 1 in which said emitter comprises:
   (a) an upper exterior surface and an undersurface, (b) a chamber within said surfaces, said chamber having an inlet adapted to receive sterile gas from a source of sterile gas and an outlet spaced from said inlet, said outlet having a height and width predetermined to establish a height and width of a zone for shielding a surgical site from ambient airborne bacteria, and having a lower margin essentially uniformly along the outlet width equidistant to said undersurface and wherein a dimension of height between said outlet and said undersurface is such that when the emitter is affixed onto said anatomical surface the gas flow from the outlet is substantially anatomically level with the anatomical surface of the patient across the width of the outlet, (c) porous media within said chamber proximate said outlet through which sterile gas received in said inlet is passed to provide coherent non-turbulent unidirectional flow from said outlet, and (d) a shape conforming barrier in continuous contact with said undersurface along the width of said outlet for shape conforming placement of said emitter substantially anatomically levelly on an anatomical surface to prevent entrance of ambient gas between said undersurface of said emitter and said anatomical surface.

3. The emitter of claim 2 in which said emitter further comprises a flat surface on at least a portion of said upper exterior surface of said emitter providing a tray for placement of surgical instruments, and a gas vent from the interior of said assembly facing and opening across said tray for passing sterile gas across said tray to maintain a sterile field on said tray for said instruments.

4. The apparatus of claim 2 in which the underside of the emitter is incurvate.

5. The apparatus of claim 2 in which said barrier is compressible.

6. The apparatus of claim 2 in which said porous media is situated within said chamber proximate said outlet through which sterile gas received in said emitter inlet is passed, said apparatus further comprising flow guides inside said emitter between said emitter inlet and said emitter outlet, placed for distributing sterile gas evenly across said porous media.

7. The apparatus of claim 2, further comprising:

(a) a hose for attachment distally to a source of sterile gas and proximately to said emitter inlet, said hose having a flexibility allowing the emitter to be placed substantially anatomically levelly directly on a portion of a patient's surface anatomy adjacent and all to one side of said site of surgical incision, and (b) at least one releasable fastener for releasably affixing said emitter to said portion of anatomy substantially anatomically levelly and in anatomically shape conforming contact therewith.

8. The apparatus of claim 7 in which said fastener comprises an adhesive strip on the side of said barrier to be placed on said portion of anatomy.

9. The apparatus of claim 7 in which said fastener comprises at least one strap and strap fastener affixed to said emitter.

10. The apparatus of claim 1 in which said emitter has an undersurface so matching the shape of said anatomical surface that when said emitter is affixed to said anatomical surface ambient airflow is substantially completely prevented from penetrating underneath the emitter and entering the interior of said coherent non-turbulent flow.

11. The apparatus of claim 10 in which said emitter has an outlet for said sterile gas having a dimension of height and width and has a lower margin essentially uniformly along the outlet width equidistant to said undersurface and wherein a dimension of height between said outlet and said undersurface is such that when the emitter is affixed onto said anatomical surface the gas flow from the outlet is substantially anatomically level with the anatomical surface of the patient across the width of the outlet.

12. The apparatus of claim 11 comprising a shape conforming barrier in continuous contact with said at least a portion of said undersurface under said outlet along a width of said outlet for shape conforming placement of said emitter directly on said anatomical surface to prevent entrance of ambient air between said underside and said anatomical surface.

13. The apparatus of claim 12 in which said shape conforming barrier is deformable.

14. The apparatus of claim 13 in which said shape conforming barrier is a compressible foam material adhered to said portion of said undersurface of the emitter.

15. The apparatus of claim 11 in which the emitter comprises a molded emitter body that generally conforms to a typical shape of an anatomical surface adjacent a said site and a shape conformable material affixed to the underside of the molded body to provide a barrier substantially completely preventing infiltration of ambient airflow underneath the emitter when the emitter is affixed on the anatomical surface.

16. The apparatus of claim 15 in which the emitter has an underside that is incurvate and an outlet for the gas flow that has a correspondingly incurvate lower margin.

17. The apparatus of claim 15 comprising adhesive on an undersurface of said shape conformable material for releasably affixing said emitter to said anatomical surface.

18. The apparatus of claim 15 comprising one or more straps for strapping said emitter to said anatomical surface.

19. Apparatus for protecting a site of surgical incision in the anatomy of a patient from ambient airborne microbes in an operating room in which the site is exposed to the operating room atmosphere during surgery, comprising an anatomically shape conformable emitter configured (i) to emit sterile coherent non-turbulent gas, in one direction only, into ambient air in the operating room, substantially anatomically levelly with the anatomical surface of the patient adjacent only one side of said site for flow of the emitted sterile coherent non-turbulent gas substantially anatomically levelly across the site unidirectionally from said one side of the site to an opposite side thereof, and (ii) to block entry of ambient air under said emitter into said flow, said emitter comprising:

(a) an upper exterior surface and an undersurface, (b) a chamber within said surfaces, said chamber having an inlet adapted to receive sterile gas from a source of sterile gas and an outlet spaced from said inlet, said outlet having a height and width predetermined to establish a height and width of a zone for shielding a surgical site from ambient airborne bacteria, and having a lower margin essentially uniformly along the outlet width equidistant to said undersurface and wherein a dimension of height between said outlet and said undersurface is such that when the emitter is affixed onto said anatomical surface the gas flow from the outlet is substantially anatomically level with the anatomical surface of the patient across the width of the outlet, (c) porous media within said chamber proximate said outlet through which sterile gas received in said inlet is passed to provide coherent non-turbulent unidirectional flow from said outlet, (d) a shape conforming barrier in continuous contact with said undersurface along the width of said outlet for shape conforming placement of said emitter substantially anatomically levelly on an anatomical surface to prevent entrance of ambient gas between said undersurface of said emitter and said anatomical surface, and (e) a flat surface on at least a portion of said upper exterior surface of said emitter providing a tray for placement of surgical instruments, and (vi) a gas vent from said chamber facing and opening across said tray for passing sterile gas across said tray to maintain a sterile field on said tray for said instruments.

* * * * *